US 10,426,359 B2

(12) United States Patent
Gopalakrishnan et al.

(10) Patent No.: US 10,426,359 B2
(45) Date of Patent: Oct. 1, 2019

(54) METHODS AND SYSTEMS FOR ARRHYTHMIA TRACKING AND SCORING

(71) Applicant: AliveCor, Inc.

(72) Inventors: Ravi Gopalakrishnan, San Francisco, CA (US); Lev Korzinov, San Francisco, CA (US); Fei Wang, San Francisco, CA (US); Euan Thomson, Los Gatos, CA (US); Nupur Srivastava, San Francisco, CA (US); Omar Dawood, San Francisco, CA (US); Iman Abuzeid, San Francisco, CA (US); David E. Albert, Oklahoma City, OK (US)

(73) Assignee: AliveCor, Inc., Mountain View, CA (US)

( * ) Notice: Subject to any disclaimer, the term of this patent is extended or adjusted under 35 U.S.C. 154(b) by 0 days.

(21) Appl. No.: 16/153,446

(22) Filed: Oct. 5, 2018

(65) Prior Publication Data

US 2019/0038149 A1 Feb. 7, 2019

Related U.S. Application Data

(63) Continuation of application No. 15/393,077, filed on Dec. 28, 2016, now Pat. No. 10,159,415, which is a (Continued)

(51) Int. Cl.
*A61B 5/02* (2006.01)
*A61B 5/0205* (2006.01)
(Continued)

(52) U.S. Cl.
CPC ........ *A61B 5/02055* (2013.01); *A61B 5/0022* (2013.01); *A61B 5/0245* (2013.01); *A61B 5/02405* (2013.01); *A61B 5/02416* (2013.01); *A61B 5/046* (2013.01); *A61B 5/681* (2013.01); *A61B 5/6898* (2013.01); *A61B 5/7264* (2013.01); *A61B 5/7275* (2013.01);
(Continued)

(58) Field of Classification Search
USPC .......................................... 600/483, 508–509
See application file for complete search history.

(56) References Cited

U.S. PATENT DOCUMENTS

| | | | |
|---|---|---|---|
| 2007/0213624 A1* | 9/2007 | Reisfeld | A61B 5/0402 600/504 |
| 2012/0197148 A1* | 8/2012 | Levitan | A61B 5/02405 600/515 |
| 2014/0125619 A1* | 5/2014 | Panther | G06F 3/04883 345/173 |

* cited by examiner

*Primary Examiner* — Nicole F Lavert
(74) *Attorney, Agent, or Firm* — Womble Bond Dickinson (US) LLP

(57) ABSTRACT

A dashboard centered around arrhythmia or atrial fibrillation tracking is provided. The dashboard includes a heart or cardiac health score that can be calculated in response to data from the user such as their ECG and other personal information and cardiac health influencing factors. The dashboard also provides to the user recommendations or goals, such as daily goals, for the user to meet and thereby improve their heart or cardiac health score. These goals and recommendations may be set by the user or a medical professional and routinely updated as his or her heart or cardiac health score improves or otherwise changes. The dashboard is generally displayed from an application provided on a smartphone or tablet computer of the user.

33 Claims, 16 Drawing Sheets

Related U.S. Application Data continuation of application No. 14/730,122, filed on Jun. 3, 2015, now Pat. No. 9,572,499, which is a continuation of application No. 14/569,513, filed on Dec. 12, 2014, now Pat. No. 9,420,956.

(60) Provisional application No. 62/014,516, filed on Jun. 19, 2014, provisional application No. 61/970,551, filed on Mar. 26, 2014, provisional application No. 61/969,019, filed on Mar. 21, 2014, provisional application No. 61/953,616, filed on Mar. 14, 2014, provisional application No. 61/915,113, filed on Dec. 12, 2013.

(51) Int. Cl.
*A61B 5/024* (2006.01)
*A61B 5/0245* (2006.01)
*A61B 5/046* (2006.01)
*A61B 5/00* (2006.01)
*G06F 19/00* (2018.01)
*G16H 20/40* (2018.01)
*G16H 15/00* (2018.01)
*G16H 10/60* (2018.01)
*A61B 5/021* (2006.01)
*A61B 5/0452* (2006.01)
*A61B 5/11* (2006.01)
*G16H 50/30* (2018.01)
*G16H 40/63* (2018.01)

(52) U.S. Cl.
CPC .............. *A61B 5/746* (2013.01); *G06F 19/00* (2013.01); *G06F 19/3418* (2013.01); *G16H 20/40* (2018.01); *A61B 5/021* (2013.01); *A61B 5/02438* (2013.01); *A61B 5/0452* (2013.01); *A61B 5/1118* (2013.01); *G06F 19/3481* (2013.01); *G16H 10/60* (2018.01); *G16H 15/00* (2018.01); *G16H 40/63* (2018.01); *G16H 50/30* (2018.01)

METHODS AND SYSTEMS FOR ARRHYTHMIA TRACKING AND SCORING

CROSS-REFERENCE TO RELATED APPLICATIONS

This application is a continuation of U.S. application Ser. No. 15/393,077, filed Dec. 28, 2016, which is a continuation of U.S. application Ser. No. 14/730,122, filed Jun. 3, 2015, now U.S. Pat. No. 9,572,499, issued Feb. 21, 2017, which is a continuation of U.S. application Ser. No. 14/569,513 filed Dec. 12, 2014, now U.S. Pat. No. 9,420,956, issued Aug. 23, 2016, which claims the benefit of U.S. Provisional Application No. 61/915,113, filed Dec. 12, 2013, which application is incorporated herein by reference, U.S. Provisional Application No. 61/953,616 filed Mar. 14, 2014, U.S. Provisional Application No. 61/969,019, filed Mar. 21, 2014, U.S. Provisional Application No. 61/970,551 filed Mar. 26, 2014 which application is incorporated herein by reference, and U.S. Provisional Application No. 62/014,516, filed Jun. 19, 2014, which application is incorporated herein by reference

BACKGROUND

The present disclosure relates to medical devices, systems, and methods. In particular, the present disclosure relates to methods and systems for managing health and disease such as cardiac diseases including arrhythmia and atrial fibrillation.

Cardiovascular diseases are the leading cause of death in the world. In 2008, 30% of all global death can be attributed to cardiovascular diseases. It is also estimated that by 2030, over 23 million people will die from cardiovascular diseases annually. Cardiovascular diseases are prevalent in the populations of high-income and low-income countries alike.

Arrhythmia is a cardiac condition in which the electrical activity of the heart is irregular or is faster (tachycardia) or slower (bradycardia) than normal. Although many arrhythmias are not life-threatening, some can cause cardiac arrest and even sudden cardiac death. Atrial fibrillation is the most common cardiac arrhythmia. In atrial fibrillation, electrical conduction through the ventricles of heart is irregular and disorganized. While atrial fibrillation may cause no symptoms, it is often associated with palpitations, shortness of breath, fainting, chest, pain or congestive heart failure. Atrial fibrillation is also associated with atrial clot formation, which is associated with clot migration and stroke.

Atrial fibrillation is typically diagnosed by taking an electrocardiogram (ECG) of a subject, which shows a characteristic atrial fibrillation waveform To treat atrial fibrillation, a patient may take medications to slow heart rate or modify the rhythm of the heart. Patients may also take anticoagulants to prevent atrial clot formation and stroke. Patients may even undergo surgical intervention including cardiac ablation to treat atrial fibrillation.

Often, a patient with arrhythmia or atrial fibrillation is monitored for extended periods of time to manage the disease. For example, a patient may be provided with a Holter monitor or other ambulatory electrocardiography device to continuously monitor a patient's heart rate and rhythm for at least 24 hours.

Current ambulatory electrocardiography devices such as Holter monitors, however, are typically bulky and difficult for subjects to administer without the aid of a medical professional. For example, the use of Holter monitors requires a patient to wear a bulky device on their chest and precisely place a plurality of electrode leads on precise locations on their chest. These requirements can impede the activities of the subject, including their natural movement, bathing, and showering. Once an ECG is generated, the ECG is sent to the patient's physician who may analyze the ECG and provide a diagnosis and other recommendations. Currently, this process often must be performed through hospital administrators and health management organizations and many patients do not receive feedback in an expedient manner.

SUMMARY

Disclosed herein are devices, systems, and methods for managing health and disease such as cardiac diseases, including arrhythmia and atrial fibrillation. In particular, a cardiac disease and/or rhythm management system, according to aspects of the present disclosure, allows a user to conveniently document their electrocardiograms (ECG) and other biometric data and receive recommendation(s) and/or goal(s) generated by the system or by a physician in response to the documented data. The cardiac disease and/or rhythm management system can be loaded onto a local computing device of the user, where biometric data can be conveniently entered onto the system while the user may continue to use the local computing device for other purposes. A local computing device may comprise, for example, a computing device worn on the body (e.g. a head-worn computing device such as a Google Glass, a wrist-worn computing device such as a Samsung Galaxy Gear Smart Watch, etc.), a tablet computer (e.g. an Apple iPad, an Apple iPod, a Google Nexus tablet, a Samsung Galaxy Tab, a Microsoft Surface, etc.), a smartphone (e.g. an Apple iPhone, a Google Nexus phone, a Samsung Galaxy phone, etc.)

A portable computing device or an accessory thereof may be configured to continuously measure one or more physiological signals of a user. The heart rate of the user may be continuously measured. The continuously measurement may be made with a wrist or arm band or a patch in communication with the portable computing device. The portable computing device may have loaded onto (e.g. onto a non-transitory computer readable medium of the computing device) and executing thereon (e.g. by a processor of the computing device) an application for one or more of receiving the continuously measured physiological signal(s), analyzing the physiological signal(s), sending the physiological signal(s) to a remote computer for further analysis and storage, and displaying to the user analysis of the physiological signal(s). The heart rate may be measured by one or more electrodes provided on the computing device or accessory, a motion sensor provided on the computing device or accessory, or by imaging and lighting sources provided on the computing device or accessory. In response to the continuous measurement and recordation of the heart rate of the user, parameters such as heart rate (HR), heart rate variability (R-R variability or HRV), and heart rate turbulence (HRT) may be determined. These parameters and further parameters may be analyzed to detect and/or predict one or more of atrial fibrillation, tachycardia, bradycardia, bigeminy, trigeminy, or other cardiac conditions. A quantitative heart health score may also be generated from the determined parameters. One or more of the heart health score, detected heart conditions, or recommended user action items based on the heart health score may be displayed to the user through a display of the portable computing device.

The biometric data may be uploaded onto a remote server where one or more cardiac technicians or cardiac specialists may analyze the biometric data and provide ECG interpretations, diagnoses, recommendations such as lifestyle recommendations, and/or goals such as lifestyle goals for subject. These interpretations, diagnoses, recommendations, and/or goals may be provided to the subject through the cardiac disease and/or rhythm management system on their local computing device. The cardiac disease and/or rhythm management system may also include tools for the subject to track their biometric data and the associated interpretations, diagnoses, recommendations, and/or goals from the cardiac technicians or specialists.

An aspect of the present disclosure includes a dashboard centered around arrhythmia or atrial fibrillation tracking. The dashboard includes a heart score that can be calculated in response to data from the user such as their ECG and other personal information such as age, gender, height, weight, body fat, disease risks, etc. The main driver of this heart score will often be the incidence of the user's atrial fibrillation. Other drivers and influencing factors include the aforementioned personal information. The heart score will be frequently related to output from a machine learning algorithm that combines and weights many if not all of influencing factors.

The dashboard will often display and track many if not all of the influencing factors. Some of these influencing factors may be entered directly by the user or may be input by the use of other mobile health monitoring or sensor devices. The user may also use the dashboard as an atrial fibrillation or arrhythmia management tool to set goals to improve their heart score.

The dashboard may also be accessed by the user's physician (e.g. the physician prescribing the system to the user, another regular physician, or other physician) to allow the physician to view the ECG and biometric data of the user, view the influencing factors of the user, and/or provide additional ECG interpretations, diagnoses, recommendations, and/or goals.

Another aspect of the present disclosure provides a method for managing cardiac health. Biometric data of a user may be received. A cardiac health score may be generated in response to the received biometric data. One or more recommendations or goals for improving the generated cardiac health score may be displayed to the user. The biometric data may comprise one or more of an electrocardiogram (ECG), dietary information, stress level, activity level, gender, height, weight, age, body fat percentage, blood pressure, results from imaging scans, blood chemistry values, or genotype data. The recommendations or goals may be updated in response to the user meeting the displayed recommendations or goals. The user may be alerted if one or more recommendations or goals have not been completed by the user, for example if the user has not completed one or more recommendations or goals for the day.

The analysis applied may be through one or more of the generation of a heart health score or the application of one or more machine learning algorithms. The machine learning algorithms may be trained using population data of heart rate. The population data may be collected from a plurality of the heart rate monitoring enabled portable computing devices or accessories provided to a plurality of users. The training population of users may have been previously identified as either having atrial fibrillation or not having atrial fibrillation prior to the generation of data for continuously measured heart rate. The data may be used to train the machine learning algorithm to extract one or more features from any continuously measured heart rate data and identify atrial fibrillation or other conditions therefrom. After the machine learning algorithm has been trained, the machine learning algorithm may recognize atrial fibrillation from the continuously measured heart rate data of a new user who has not yet been identified as having atrial fibrillation or other heart conditions. One or more of training population data or the trained machine learning algorithm may be provided on a central computing device (e.g. be stored on a non-transitory computer readable medium of a server) which is in communication with the local computing devices of the users and the application executed thereon (e.g. through an Internet or an intranet connection.)

A set of instructions for managing cardiac health may be downloaded from the Internet. These set of instructions may be configured to automatically generate the cardiac health score. The cardiac health score may be generated using a machine learning algorithm. The machine learning algorithm may generate the cardiac health score of the user and/or the recommendations and/or goals in response to biometric data from a plurality of users. The set of instructions may be configured to allow a medical professional to access the received biometric data. The cardiac health score and/or the recommendations and/or goals may be generated by the medical professional.

The set of instructions may be stored on a non-transitory computer readable storage medium of one or more of a body-worn computer, a tablet computer, a smartphone, or other computing device. These set of instructions may be capable of being executed by the computing device. When executed, the set of instructions may cause the computing device to perform any of the methods described herein, including the method for managing cardiac health described above.

Another aspect of the present disclosure provides a system for managing cardiac health. The system may comprise a sensor for recording biometric data of a user and a local computing device receiving the biometric data from the sensor. The local computing device may be configured to display a cardiac health score and one or more recommendations or goals for the user to improve the cardiac health score in response to the received biometric data.

The system may further comprise a remote server receiving the biometric data from the local computing device. One or more of the local computing device or the remote server may comprise a machine learning algorithm which generates one or more of the cardiac health score or the one or more recommendations or goals for the user. The remote server may be configured for access by a medical professional. Alternatively or in combination, one or more of the cardiac health score or one or more recommendations or goals may be generated by the medical professional and provided to the local computing device through the remote server.

The sensor may comprise one or more of a hand-held electrocardiogram (ECG) sensor, a wrist-worn activity sensor, a blood pressure monitor, a personal weighing scale, a body fat percentage sensor, a personal thermometer, a pulse oximeter sensor, or any mobile health monitor or sensor. Often, the sensor is configured to be in wireless communication with the local computing device. The local computing device comprises one or more of a personal computer, a laptop computer, a palmtop computer, a tablet computer, a smartphone, a body-worn computer, or the like. The biometric data may comprise one or more of an electrocardiogram (ECG), dietary information, stress level, activity level, gender, height, weight, age, body fat percentage, or blood pressure.

Other physiological signals or parameters such as physical activity, heart sounds, blood pressure, blood oxygenation, blood glucose, temperature, activity, breath composition, weight, hydration levels, an electroencephalograph (EEG), an electromyography (EMG), a mechanomyogram (MMG), an electrooculogram (EOG), etc. may also be monitored. The user may also input user-related health data such as age, height, weight, body mass index (BMI), diet, sleep levels, rest levels, or stress levels. One or more of these physiological signals and/or parameters may be combined with the heart rate data to detect atrial fibrillation or other conditions. The machine learning algorithm may be configured to identify atrial fibrillation or other conditions in response to heart rate data in combination with one or more of the other physiological signals and/or parameters for instance. Triggers or alerts may be provided to the user in response to the measured physiological signals and/or parameters. Such triggers or alerts may notify the user to take corrective steps to improve their health or monitor other vital signs or physiological parameters. The application loaded onto and executed on the portable computing device may provide a health dash board integrating and displaying heart rate information, heart health parameters determined in response to the heart rate information, other physiological parameters and trends thereof, and recommended user action items or steps to improve health.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the subject matter disclosed herein are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION

Devices, systems, and methods for managing health and disease such as cardiac diseases, including arrhythmia and atrial fibrillation, are disclosed. In particular, a cardiac disease and/or rhythm management system, according to aspects of the present disclosure, allows a user to conveniently document their electrocardiograms (ECG) and other biometric data and receive recommendation(s) and/or goal(s) generated by the system or by a physician in response to the documented data.

The term "atrial fibrillation," denoting a type of cardiac arrhythmia, may also be abbreviated in either the figures or description herein as "AFIB."

Figure 1:
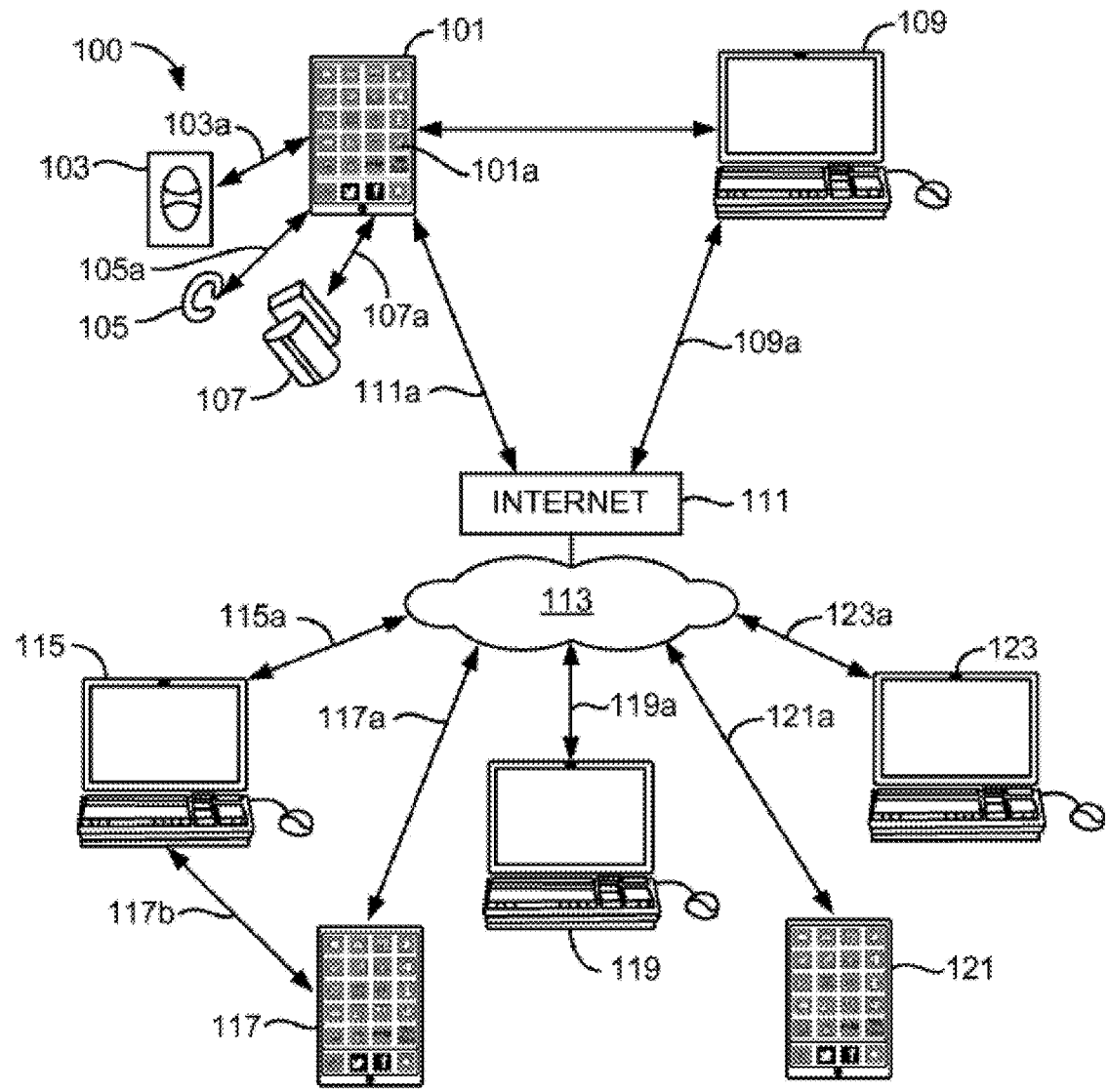
FIG. 1 shows a system for cardiac disease and rhythm management.

FIG. 1 shows a system 100 for cardiac disease and rhythm management. The system 100 may be prescribed for use by a user or subject such as being prescribed by the user or subject's regular or other physician or doctor. The system 100 may comprise a local computing device 101 of the user or subject. The local computing device 101 may be loaded with a user interface, dashboard, or other sub-system of the cardiac disease and rhythm management system 100. For example, the local computing device 101 may be loaded with a mobile software application ("mobile app") 101a for interfacing with the system 100. The local computing device may comprise a computing device worn on the body (e.g. a head-worn computing device such as a Google Glass, a wrist-worn computing device such as a Samsung Galaxy Gear Smart Watch, etc.), a tablet computer (e.g. an Apple iPad, an Apple iPod, a Google Nexus tablet, a Samsung Galaxy Tab, a Microsoft Surface, etc.), a smartphone (e.g. an Apple iPhone, a Google Nexus phone, a Samsung Galaxy phone, etc.).

The local computing device 101 may be coupled to one or more biometric sensors. For example, the local computing device 101 may be coupled to a handheld ECG monitor 103. The handheld ECG monitor 103 may be in the form of a smartphone case as described in co-owned U.S. patent application Ser. No. 12/796,188 (now U.S. Pat. No. 8,509,882), Ser. Nos. 13/107,738, 13/420,520 (now U.S. Pat. No. 8,301,232), Ser. Nos. 13/752,048, 13/964,490, 13/969,446, 14/015,303, and 14/076,076, the contents of which are incorporated herein by reference.

In some embodiments, the handheld ECG monitor 103 may be a handheld sensor coupled to the local computing device 101 with an intermediate protective case/adapter as described in U.S. Provisional Application No. 61/874,806, filed Sep. 6, 2013, the contents of which are incorporated herein by reference. The handheld ECG monitor 103 may be used by the user to take an ECG measurement which the handheld ECG monitor 103 may send to the local computing device by connection 103a. The connection 103a may comprise a wired or wireless connection (e.g. a WiFi connection, a Bluetooth connection, a NFC connection, an ultrasound signal transmission connection, etc.). The mobile software application 101a may be configured to interface with the one or more biometric sensors including the handheld ECG monitor 103.

The local computing device 101 may be coupled to a wrist-worn biometric sensor 105 through a wired or wireless connection 105a (e.g. a WiFi connection, a Bluetooth connection, a NFC connection, an ultrasound signal transmission connection, etc.). The wrist-worn biometric sensor 105 may comprise an activity monitor such as those available from Fitbit Inc. of San Francisco, Calif. or a Nike FuelBand available from Nike, Inc. of Oregon. The wrist-worn biometric sensor 105 may also comprise an ECG sensor such as that described in co-owned U.S. Provisional Application No. 61/872,555, the contents of which is incorporated herein by reference.

The local computing device 101 may be coupled to other biometric devices as well such as a personal scale or a blood pressure monitor 107. The blood pressure monitor 107 may communicate with the local device 101 through a wired or wireless connection 107a (e.g. a WiFi connection, a Bluetooth connection, a NFC connection, an ultrasound signal transmission connection, etc.).

The local computing device 101 may directly communicate with a remote server or cloud-based service 113 through the Internet 111 via a wired or wireless connection 111a (e.g. a WiFi connection, a cellular network connection, a DSL Internet connection, a cable Internet connection, a fiber optic Internet connection, a T1 Internet connection, a T3 Internet connection, etc.). Alternatively or in combination, the local computing device 101 may first couple with another local computing device 109 of the user, such as a personal computer of the user, which then communicates with the remote server or cloud-based service 113 via a wired or wireless connection 109a (e.g. a WiFi connection, a cellular network connection, a DSL Internet connection, a cable Internet connection, a fiber optic Internet connection, a T1 Internet connection, a T3 Internet connection, etc.) The local computing device 109 may comprise software or other interface for managing biometric data collected by the local computing device 101 or the biometric data dashboard loaded on the local computing device 101.

Other users may access the patient data through the remote server or cloud-based service 113. These other users may include the user's regular physician, the user's pre-scribing physician who prescribed the system 100 for use by the user, other cardiac technicians, other cardiac specialists, and system administrators and managers. For example, a first non-subject user may access the remote server or cloud-based service 113 with a personal computer or other computing device 115 through an Internet connection 115a (e.g. a WiFi connection, a cellular network connection, a DSL Internet connection, a cable Internet connection, a fiber optic Internet connection, a T1 Internet connection, a T3 Internet connection, etc.). Alternatively or in combination, the first non-subject user may access the remote server or cloud-based service 113 with a local computing device such as a tablet computer or smartphone 117 through an Internet connection 117a. The tablet computer or smartphone 117 of the first non-subject user may interface with the personal computer 115 through a wired or wireless connection 117b (e.g. a WiFi connection, a Bluetooth connection, a NFC connection, an ultrasound signal transmission connection, etc.). Further, a second non-subject user may access the remote server or cloud-based service 113 with a personal computer or other computing device 119 through an Internet connection 119a (e.g. a WiFi connection, a cellular network connection, a DSL Internet connection, a cable Internet connection, a fiber optic Internet connection, a T1 Internet connection, a T3 Internet connection, etc.). Further, a third non-subject user may access the remote server or cloud-based service 113 with a tablet computer or smartphone 121 through an Internet connection 121a (e.g. a WiFi connection, a cellular network connection, a DSL Internet connection, a cable Internet connection, a fiber optic Internet connection, a T1 Internet connection, a T3 Internet connection, etc.). Further, a fourth non-subject user may access the remote server or cloud-based service 113 with a personal computer or other computing device 123 through an Internet connection 123a (e.g. a WiFi connection, a cellular network connection, a DSL Internet connection, a cable Internet connection, a fiber optic Internet connection, a T1 Internet connection, a T3 Internet connection, etc.). The first non-subject user may comprise an administrator or manager of the system 100. The second non-subject user may comprise a cardiac technician. The third non-subject user may comprise a regular or prescribing physician of the user or subject. And, the fourth non-subject user may comprise a cardiac specialist who is not the user or subject's regular or prescribing physician. Generally, many if not all of the communication between various devices, computers, servers, and cloud-based services will be secure and HIPAA-compliant.

Aspects of the present disclosure provide systems and methods for detecting and/or predicting atrial fibrillation or other arrhythmias of a user by applying one or more machine learning-based algorithms. A portable computing device (or an accessory usable with the portable computing device) may provide R-R intervals and/or raw heart rate signals as input to an application loaded and executed on the portable computing device. The raw heart rate signals may be provided using an electrocardiogram (ECG) in communication with the portable computing device or accessory such as described in U.S. Ser. No. 13/964,490 filed Aug. 12, 2013, Ser. No. 13/420,520 filed Mar. 14, 2013, Ser. No. 13/108,738 filed May 16, 2011, and Ser. No. 12/796,188 filed Jun. 8, 2010. Alternatively or in combination, the raw heart rate signals may be provided using an on-board heart rate sensor of the portable computing device or by using photoplethysmography implemented by an imaging source and a light source of the portable computing device. Alternatively or in combination, the raw heart rate signals may be from an accessory device worn by the user or attached to the user (e.g. a patch) and which is in communication with the portable computing device. Such wearable accessory devices may include Garmin's Vivofit Fitness Band, Fitbit, Polar Heart Rate Monitors, New Balance's Balance Watch, Basis B1 Band, MIO Alpha, Withings Pulse, LifeCORE Heart Rate Monitor strap, and the like.

R-R intervals may be extracted from the raw heart rate signals. The R-R intervals may be used to calculate heart rate variability (HRV) which may be analyzed in many ways such as using time-domain methods, geometric methods, frequency-domain methods, non-linear methods, long term correlations, or the like as known in the art. Alternatively or in combination, the R-R intervals may be used for non-traditional measurements such as (i) determining the interval between every other or every three R-waves to evaluate for bigeminy or trigeminy or (ii) the generation of a periodic autoregressive moving average (PARMA).

The machine learning based algorithm(s) may allow software application(s) to identify patterns and/or features of the R-R interval data and/or the raw heart rate signals or data to predict and/or detect atrial fibrillation or other arrhythmias. These extracted and labelled features may be features of HRV as analyzed in the time domain such as SDNN (the standard deviation of NN intervals calculated over a 24 hour period), SDANN (the standard deviation of the average NN intervals calculated over short periods), RMSSD (the square root of the mean of the sum of the squares of the successive differences between adjacent NNs), SDSD (the standard deviation of the successive differences between adjacent NNs), NN50 (the number of pairs of successive NNs that differ by more than 50 ms), pNN50 (the proportion of NN50 divided by total number of NNs), NN20 (the number of pairs of successive NNs that differ by more than 20 ms), pNN20 (the proportion of NN20 divided by the total number of NNs), EBC (estimated breath cycle), NNx (the number of pairs of successive NNs that differ by more than x ms), pNNx (the proportion of NNx divided by the number of NNs), or other features known in the art. Alternatively or in combination, the extracted and labelled features may comprise a nonlinear transform of R-R ratio or R-R ratio statistics with an adaptive weighting factor. Alternatively or in combination, the extracted and labelled features may be features of HRV as analyzed geometrically such as the sample density distribution of NN interval durations, the sample density distribution of differences between adjacent NN intervals, a Lorenz plot of NN or RR intervals, degree of skew of the density distribution, kurtosis of the density distribution, or other features known in the art. Alternatively or in combination, the extracted and labelled features may be features of HRV in the frequency domain such as the power spectral density of different frequency bands including a high frequency band (HF, from 0.15 to 0.4 Hz), low frequency band (LF, from 0.04 to 0.15 Hz), and the very low frequency band (VLF, from 0.0033 to 0.04 Hz), or other frequency domain features as known in the art. Alternatively or in combination, the extracted and labelled features may be non-linear features such as the geometric shapes of a Poincaré plot, the correlation dimension, the nonlinear predictability, the pointwise correlation dimension, the approximate entropy, and other features as known in the art. Other features from the raw heart rate signals and data may also be analyzed. These features include for example a generated autoregressive (AR) model, a ratio of consecutive RR intervals, a normalized ratio of consecutive RR intervals, a standard deviation of every 2, 3, or 4 RR intervals, or a recurrence plot of the raw HR signals, among others.

The features of the analysis and/or measurement may be selected, extracted, and labelled to predict atrial fibrillation or other arrhythmias in real time, e.g. by performing one or more machine learning operation. Such operations can be selected from among an operation of ranking the feature(s), classifying the feature(s), labelling the feature(s), predicting the feature(s), and clustering the feature(s). Alternatively or in combination, the extracted features may be labelled and saved for offline training of a machine learning algorithm or set of machine learning operations. For example, the operations may be selected from any of those above. Any number of machine learning algorithms or methods may be trained to identify atrial fibrillation or other conditions such as arrhythmias. These may include the use of decision tree learning such as with a random forest, association rule learning, artificial neural network, inductive logic programming, support vector machines, clustering, Bayesian networks, reinforcement learning, representation learning, similarity and metric learning, sparse dictionary learning, or the like.

The systems and methods for detecting and/or predicting atrial fibrillation or other conditions such as arrhythmias described herein may be implemented as software provided as a set of instructions on a non-transitory computer readable medium. A processor of a computing device (e.g. a tablet computer, a smartphone, a smart watch, a smart band, a wearable computing device, or the like) may execute this set of instructions to receive the input data and detect and/or predict atrial fibrillation therefrom. The software may be downloaded from an online application distribution platform such as the Apple iTunes or App Store, Google Play, Amazon App Store, and the like. A display of the computing device may notify the user whether atrial fibrillation or other arrhythmias has been detected and/or if further measurements are required (e.g. to perform a more accurate analysis). The software may be loaded on and executed by the portable computing device of the user such as with the processor of the computing device.

The machine learning-based algorithms or operations for predicting and/or detecting atrial fibrillation or other arrhythmias may be provided as a service from a remote server which may interact or communicate with a client program provided on the computing device of the user, e.g. as a mobile app. The interaction or communication may be through an Application Program Interface (API). The API may provide access to machine learning operations for ranking, clustering, classifying, and predicting from the R-R interval and/or raw heart rate data, for example.

The machine learning-based algorithms or operations, provided through a remote server and/or on a local application on a local computing device, may operate on, learn from, and make analytical predictions from R-R interval data or raw heart rate data, e.g. from a population of users. The R-R interval or raw heart rate data may be provided by the local computing device itself or an associated accessory, such as described in U.S. Ser. No. 13/964,490 filed Aug. 12, 2013, Ser. No. 13/420,520 filed Mar. 14, 2013, Ser. No. 13/108,738 filed May 16, 2011, and Ser. No. 12/796,188 filed Jun. 8, 2010. Thus, atrial fibrillation and other arrhythmias or other heart conditions can be in a convenient, user-accessible way.

Figure 2:
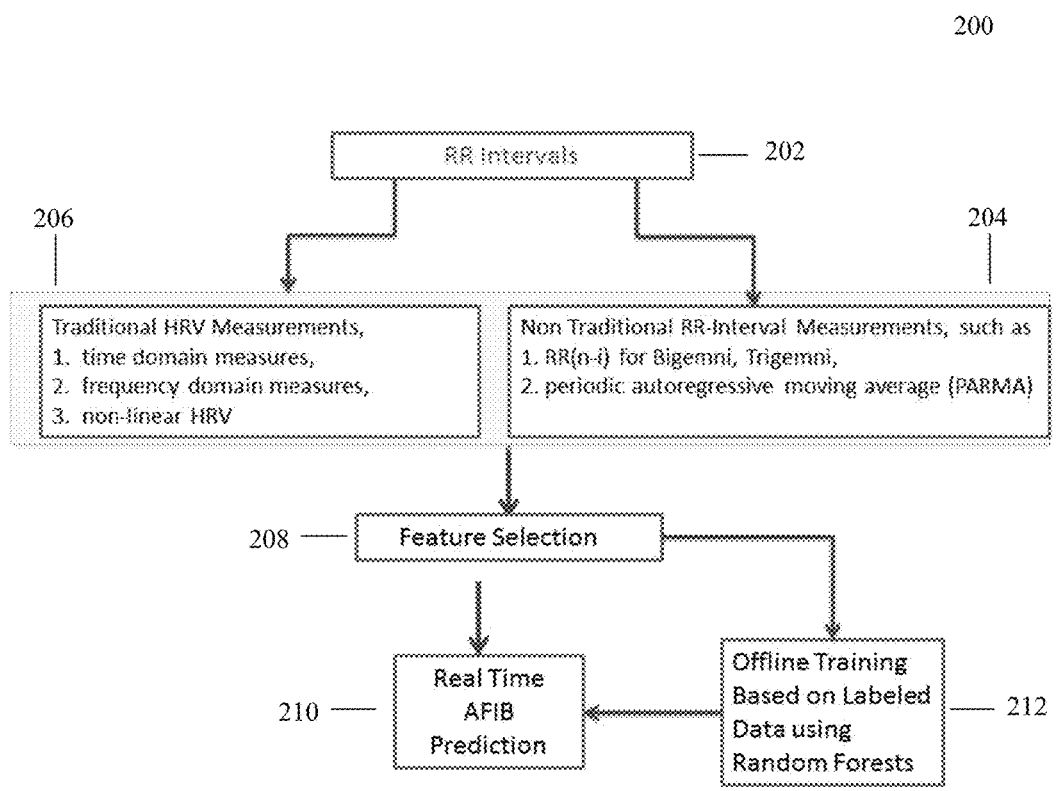
FIG. 2 shows a flow chart of a method 200 for predicting and/or detecting atrial fibrillation from R-R interval measurements.

FIG. 2 shows a flow chart of a method 200 for predicting and/or detecting atrial fibrillation from R-R interval measurements. In a step 202, an R-R interval of a user is obtained. In a step 204, the obtained R-R interval is analyzed using one or more traditional heart rate variability measurements such as, for example, time domain measures, frequency domain measures, and non-linear heart rate variability. In a step 206, the obtained R-R interval is analyzed using one or more non-traditional heart rate variability measurements such as, for example, RR (n-i) for Bigeminy and Trigeminy detection, and the generation of a periodic autoregressive moving average (PARMA). In a step 208, a feature selection occurs. In a step 210, a real time prediction or detection of atrial fibrillation, and/or in a step 212, the heart rate variability measurements may be labelled and saved for offline training of a machine learning algorithm or set of machine learning operations, and then may be subsequently used to make a real time prediction and/or detection of atrial fibrillation.

Figure 3:
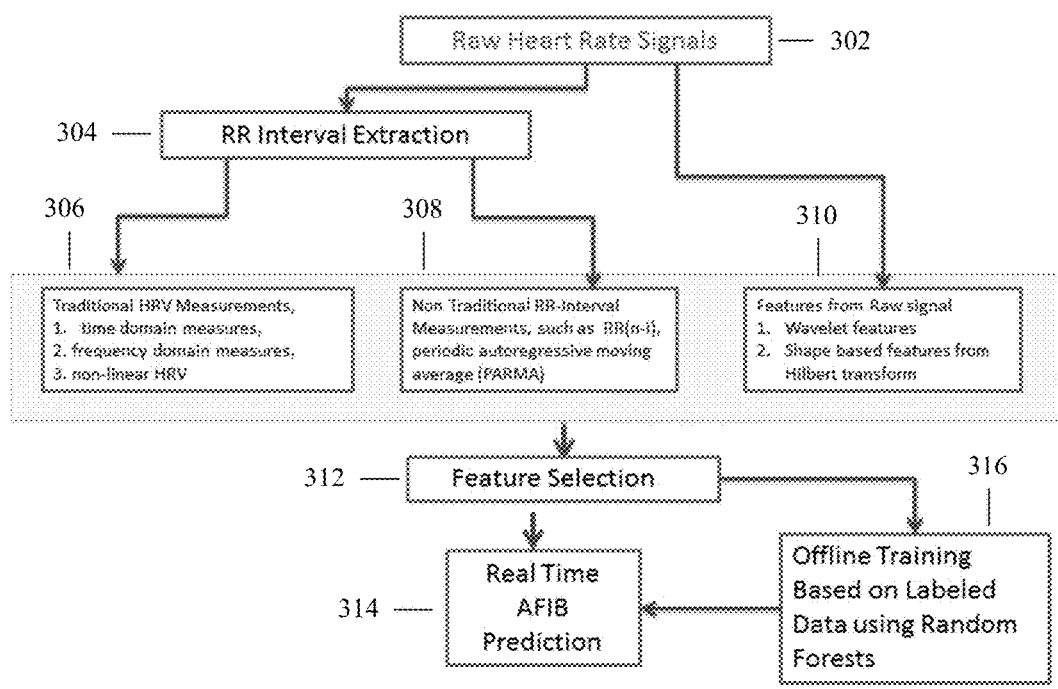
FIG. 3 shows a flow chart of a method for predicting and/or detecting atrial fibrillation from R-R interval measurements and for predicting and/or detecting atrial fibrillation from raw heart rate signals.

FIG. 3 shows a flow chart of a method 300 for predicting and/or detecting atrial fibrillation from R-R interval measurements and for predicting and/or detecting atrial fibrillation from raw heart rate signals. In a step 302, raw heart rate signals are obtained from, for example, an ECG of a user. In a step 304, R-R intervals are obtained from the obtained raw hearth signals. In a step 306, the obtained R-R interval is analyzed using one or more traditional heart rate variability measurements such as, for example, time domain measures, frequency domain measures, and non-linear heart rate variability. In a step 308, the obtained R-R interval is analyzed using one or more non-traditional heart rate variability measurements such as, for example, RR (n-i) for bigeminy and trigeminy detection, and the generation of a periodic autoregressive moving average (PARMA). In a step 310, features from the obtained heart rate features are analyzed using one or more of wavelet features and shape based features from a Hilbert transform. In a step 312, a feature selection occurs. In a step 314, a real time prediction or detection of atrial fibrillation, and/or in a step 316, the heart rate variability measurements may be labelled and saved for offline training of a machine learning algorithm or set of machine learning operations, and then may be subsequently used to make a real time prediction and/or detection of atrial fibrillation.

Although the above steps show methods 200 and 300 in accordance with many embodiments, a person of ordinary skill in the art will recognize many variations based on the teaching described herein. The steps may be completed in a different order. Steps may be added or deleted. Some of the steps may comprise sub-steps. Many of the steps may be repeated as often as beneficial to the user or subject.

One or more of the steps of method 200 and 300 may be performed with circuitry, for example, one or more of a processor or a logic circuitry such as a programmable array logic for a field programmable gate array. The circuitry may be programmed to provide one or more of the steps of methods 200 and 300, and the program may comprise program instructions stored on a non-transitory computer readable medium or memory or programmed steps of the logic circuitry such as the programmable array logic or the field programmable gate array, for example.

Aspects of the present disclosure provide systems and methods for monitoring one or more physiological parameters and providing a trigger message to the user if the one or more physiological parameter meets a pre-determined or learned threshold(s). Two or more of the physiological parameters may be combined to provide a trigger message. That is, a particular trigger message may be provided to the user if two or more pre-determined threshold(s) for the physiological parameter(s) are met.

Table 1 below shows an exemplary table of physiological parameters that may be measured (left column), features of interest to be measured or threshold types to be met (middle column), and exemplary trigger messages (right column).

TABLE 1

| Physiological Parameter | Measurements/ Threshold | Sample Trigger Messages |
| --- | --- | --- |
| Heart Rate | Heart Rate Variability (HRV), Non-linear Transformation of RR Intervals | Measure ECG; See Your Doctor |
| Heart Sound | Sound Features | Abnormal Heart Sound; Measure ECG; |

TABLE 1-continued

| Physiological Parameter | Measurements/ Threshold | Sample Trigger Messages |
| --- | --- | --- |
| Blood Pressure | Upper and Lower Thresholds | See Your Doctor High/Low Blood Pressure; Take BP Medication; Exercise; See Your Doctor |
| Blood Oxygenation | O2 Saturation, O2 Saturation Variability | High Risk of Hypoventilation; High Risk of Sleep Disorder such as Apnea; See Your Doctor |
| Blood Glucose | Upper and Lower Thresholds | High Risk of Hypoglycemia; See Your Doctor |
| Temperature | Temperature, Temperature Changes | Fever; Take OTC Fever Medication; See Your Doctor |
| Physical Activity (accelerometer data) | Gait, Chest Compressions, Speed, Distance | Monitor Senior or Infant Posture, e.g. if senior/infant has fallen |
| Electrocardiogram (ECG) | ECG Features (E.g. QT, QRS, PR intervals, HRV, etc. | High Risk of Certain Cardiac Diseases; Sleep apnea; See Your Doctor |
| Breath Content (Breathalyzer data) | Percentage of the Certain Chemicals | High Risk of Certain Dental Disease, Diabetes, etc.; See Your Doctor |

The machine learning based algorithms or operations as described herein may be used to determine the appropriate trigger thresholds in response to the raw physiological data input and/or user-input physiological parameters (e.g. age, height, weight, gender, etc.). Features of the raw physiological data input may be selected, extracted, labelled, clustered, and/or analyzed. These processed features may then be analyzed using one or more machine learning operation such as ranking the feature(s), classifying the feature(s), predicting the feature(s), and clustering the feature(s). The various machine learning algorithms described herein may be used to analyze the features to detect and predict health conditions and generate recommendations or user action items to improve the health of the user. For instance, the machine learning algorithms may be trained to identify atrial fibrillation or other conditions in response to the non-heart rate physiological parameter(s) such as age, gender, body mass index (BMI), activity level, diet, and others in combination with the raw heart rate data and HRV that can be extracted therefrom.

The systems and methods for monitoring one or more physiological parameters and providing a trigger message to the user if the one or more physiological parameter meets a pre-determined threshold(s) described herein may be implemented as software provided as a set of instructions on a non-transitory computer readable medium. A processor of a computing device (e.g. a tablet computer, a smartphone, a smart watch, a smart band, a wearable computing device, or the like) may execute this set of instructions to receive the input data and detect and/or predict atrial fibrillation therefrom. The software may be downloaded from an online application distribution platform such as the Apple iTunes or App Store, Google Play, Amazon App Store, and the like. The software may be loaded on and executed by the portable computing device of the user such as with the processor of the computing device. The software may also provide both the triggering application described herein and the heart rate monitoring and analysis for detecting atrial fibrillation or other heart conditions described herein.

In an embodiment, a method and system for longitudinal monitoring of a patient's or any consumer's (after referred to as "patient") health using various ECG monitoring devices is described herein. The ECG monitoring devices generate ECG signal data which can be stored in a database for further analysis. The ECG data, which can be stored in a database along with other patient information, can be analyzed by a processing device, such as a computer or server, using various algorithms.

Various ECG monitoring or recording devices, hereinafter referred to as ECG monitoring devices, can be used to record the ECG data. For example, the ECG monitoring device can be a handheld, portable, or wearable smartphone based device, as described in U.S. Pat. No. 8,301,232, which is herein incorporated by reference in its entirety for all purposes. A smartphone based device, or a device having wireless or cellular telecommunication capabilities, can transmit the ECG data to a database or server directly through the internet. These types of ECG monitoring devices as well as other ECG monitoring devices include portable devices, wearable recording devices, event recorders, and Holter monitors. Clinical or hospital based ECG recording devices can also be used and integrated into the system. Such devices may be able to transmit stored ECG data through a phone line or wirelessly through the internet or cellular network, or may need to be sent to a data collection center for data collection and processing. The ECG data can be tagged with the type of ECG monitoring device used to record the data by, for example, including it in metadata for indexing and searching purposes.

The ECG monitoring devices can be single lead devices or multiple lead devices, where each lead generally terminates with an electrode. Some embodiments may even be leadless and have electrodes that are integrated with the body or housing of the device, and therefore have a predetermined relationship with each other, such as a fixed spacing apart from each other. The orientation and positioning of the single lead in a single lead device or of each lead of the multiple lead device or of the electrodes of the leadless device can be transmitted with the ECG data. The lead and/or electrode placement may be predetermined and specified to the patient in instructions for using the device. For example, the patient may be instructed to position the leads and/or electrodes with references to one or more anatomical landmarks on the patient's torso. Any deviation from the predetermined lead and/or electrode placement can be notated by the patient or user when transmitting the ECG data. The lead and electrode placement may be imaged using a digital camera, which may be integrated with a smart phone, and transmitted with the ECG data and stored in the database. The lead and electrode placement may be marked on the patient's skin for imaging and for assisting subsequent placement of the leads and electrodes. The electrodes can be attached to the skin using conventional methods which may include adhesives and conducting gels, or the electrodes may simply be pressed into contact with the patient's skin. The lead and electrode placement may be changed after taking one recording or after recording for a predetermined or variable amount of time. The ECG data can be tagged with the numbers of leads and/or electrodes and the lead and/or electrode placement, including whether adhesives and/or conducting gels were used. Again, this information can be including in metadata for indexing and searching purposes.

The ECG signal data can be continuously recorded over a predetermined or variable length of time. Continuous ECG recording devices can record for up to 1, 2, 3, 4, 5, 6, 7, 8, 9, 10, 11, 12, 13, or 14 days. Alternatively or additionally, the ECG data can be recorded on demand by the patient at various discrete times, such as when the patient feels chest pains or experiences other unusual or abnormal feelings. The on demand ECG recorder can have a memory buffer that can record a predetermined amount of ECG data on a rolling basis, and when activated by the patient to record a potential event, a predetermined amount of ECG data can be saved and/or transmitted. The predetermined amount of ECG data can include a predetermined amount of ECG data before activation and a predetermined amount of ECG data after activation such that a window of ECG data is captured that encompasses the potential event. The time period between ECG recordings may be regular or irregular. For example, the time period may be once a day, once a week, once a month, or at some other predetermined interval. The ECG recordings may be taken at the same or different times of days, under similar or different circumstances, as described herein. One or more baseline ECGs can be recorded while the patient is free of symptoms. The baseline ECGs can be periodically recorded and predetermined intervals and/or on-demand. The same ECG recording device or different ECG recording devices may be used to record the various ECG of a particular patient. All this information may be tagged to or associated with the ECG data by, for example, including it in the metadata for indexing and searching purposes.

The ECG data can be time stamped and can be annotated by the patient or health care provider to describe the circumstances during which the ECG was recorded, preceding the ECG recording, and/or following the ECG recording. For example, the system and device can have an user interface for data entry that allows the patient to enter in notes regarding the conditions and circumstances surrounding the ECG recording. This additional data can be also included as metadata for indexing and searching purposes. For example, location, food, drink, medication and/or drug consumption, exercise, rest, sleep, feelings of stress, anxiety, pain or other unusual or abnormal feelings, or any other circumstance that may affect the patient's ECG signal can all be inputted into the device, smart phone, computer or other computing device to be transmitted to the server or database along with the ECG data. The annotated data can also include the patient's identity or unique identifier as well as various patient characteristics including age, sex, race, ethnicity, and relevant medical history. The annotated data can also be time stamped or tagged so that the ECG data can be matched or correlated with the activity or circumstance of interest. This also allows comparison of the ECG before, after and during the activity or circumstance so that the effect on the ECG can be determined.

The ECG data and the associated metadata can be transmitted from the device to a server and database for storage and analysis. The transmission can be real-time, at regular intervals such as hourly, daily, weekly and any interval in between, or can be on demand. The metadata facilitates the searching, organizing, analyzing and retrieving of ECG data. Comparison and analysis of a single patient's ECG data can be performed, and/or comparison of ECG data between patients can be performed. For example, the metadata can be used to identify and select a subset of ECG data where an activity or circumstance, such as the taking of medication, occurred within a predetermined amount of time to the ECG data. The components of the ECG signal data, such as the P wave, T wave, and QRS complex and the like, the amplitudes of the components, the ratios between the components, the width of the components, and the delay or time separation between the components, can be extracted, compared, analyzed, and stored as ECG features. For example, the P wave and heart rate can be extracted and analyzed to identify atrial fibrillation, where the absence of P waves and/or an irregular heart rate may indicate atrial fibrillation. The extracted ECG features can also be included in the metadata for indexing and searching.

The changes in the ECG signal over time in view of the activities and circumstances can be compared with changes over time and circumstances observed within a database of ECG's. Comparisons may include any comparison of data derived from any other ECG signal or any database of ECG's or any subset of ECG data, or with data derived from any database of ECG's. Changes in any feature of the ECG signal over time may be used for a relative comparison with similar changes in any ECG database or with data derived from an ECG database. The ECG data from the baseline ECG and the ECG data from a potential adverse event can be compared to determine the changes or deviations from baseline values. In addition, both the baseline ECG and the ECG data recorded from the patient can be compared to one or more predetermined template ECGs which can represent a normal healthy condition as well as various diseased conditions, such as myocardial infarction and arrhythmias.

The comparisons and analysis described herein can be used to draw conclusions and insights into the patient's health status, which includes potential health issues that the patient may be experiencing at the time of measurement or at future times. Conclusions and determinations may be predictive of future health conditions or diagnostic of conditions that the patient already has. The conclusions and determinations may also include insights into the effectiveness or risks associated with drugs or medications that the patient may be taking, have taken or may be contemplating taking in the future. In addition, the comparisons and analysis can be used to determine behaviors and activities that may reduce or increase risk of an adverse event. Based on the comparisons and analysis described herein, the ECG data can be classified according to a level of risk of being an adverse event. For example, the ECG data can be classified as normal, low risk, moderate risk, high risk, and/or abnormal. The normal and abnormal designation may require health care professional evaluation, diagnosis, and/or confirmation.

Diagnosis and determination of an abnormality, an adverse event, or a disease state by physicians and other health care professionals can be transmitted to the servers and database to be tagged with and associated with the corresponding ECG data. The diagnosis and determination may be based on analysis of ECG data or may be determined using other tests or examination procedures. Professional diagnosis and determinations can be extracted from the patient's electronic health records, can be entered into the system by the patient, or can be entered into the system by the medical professional. The conclusions and determinations of the system can be compared with actual diagnosis and determinations from medical professions to validate and/or refine the machine learning algorithms used by the system. The time of occurrence and duration of the abnormality, adverse event or disease state can also be included in the database, such that the ECG data corresponding with the occurrence and/or the ECG data preceding and/or following the abnormality, adverse event or disease state can be associated together and analyzed. The length of time preceding or following the abnormality may be predetermined and be up to 1 to 30 days, or greater than 1 to 12 months. Analysis of the time before the abnormality, adverse event or disease state may allow the system to identify patterns or correlations of various ECG features that precede the occurrence of the abnormality, adverse event or disease state, thereby providing advance detection or warning of the abnormality, adverse event or disease state. Analysis of the time following the abnormality, adverse event or disease state can provide information regarding the efficacy of treatments and/or provide the patient or physician information regarding disease progression, such as whether the patient's condition in improving, worsening or staying the same. The diagnosis and determination can also be used for indexing by, for example, including it in the metadata associated with the corresponding ECG data.

As described herein, various parameters may be included in the database along with the ECG data. These may include the patient's age, gender, weight, blood pressure, medications, behaviors, habits, activities, food consumption, drink consumption, drugs, medical history and other factors that may influence a patient's ECG signal. The additional parameters may or may not be used in the comparison of the changes in ECG signal over time and circumstances.

The conclusions, determinations, and/or insights into the patient's health generated by the system may be communicated to the patient directly or via the patient's caregiver (doctor or other healthcare professional). For example, the patient can be sent an email or text message that is automatically generated by the system. The email or text message can be a notification which directs the patient to log onto a secure site to retrieve the full conclusion, determination or insight, or the email or text message can include the conclusion, determination or insight. Alternatively or additionally, the email or text message can be sent to the patient's caregiver. The notification may also be provided via an application on a smartphone, tablet, laptop, desktop or other computing device.

As described herein, the system can identify behaviors, habits, activities, foods, drinks, medications, drugs, and the like which are associated with the patient's abnormal ECG readings. In addition to informing the patient of these associations, the system can provide instructions or recommendations to the patient to avoid these behaviors, habits, activities, foods, drinks, medications, drugs, and the like which are associated with the patient's abnormal ECG readings. Similarly, the system can identify behaviors, habits, activities, foods, drinks, medications, drugs, and the like which are associated with normal or improving ECG readings, and can instruct or recommend that the patient perform these behaviors, habits, and activities and/or consume these foods, drinks, medications, and drugs. The patient may avoid a future healthcare issue, as instructed or recommended by the system, by modifying their behavior, habits or by taking any course of action, including but not limited to taking a medication, drug or adhering to a diet or exercise program, which may be a predetermined course of action recommended by the system independent of any analysis of the ECG data, and/or may also result from insights learned through this system and method as described herein. In addition, the insights of the system may relate to general fitness and or mental wellbeing.

The ECG data and the associated metadata and other related data as described herein can be stored in a central database, a cloud database, or a combination of the two. The data can be indexed, searched, and/or sorted according to any of the features, parameters, or criteria described herein.

The system can analyze the ECG data of a single patient, and it can also analyze the ECG data of a group of patients, which can be selected according to any of the features, parameters or criteria described herein. When analyzing data from a single patient, it may be desirable to reduce and/or correct for the intra-individual variability of the ECG data, so that comparison of one set of ECG data taken at one particular time with another set of ECG data taken at another time reveals differences resulting from changes in health status and not from changes in the type of ECG recording device used, changes in lead and electrode placement, changes in the condition of the skin (i.e. dry, sweaty, conductive gel applied or not applied), and the like. As described above, consistent lead and electrode placement can help reduce variability in the ECG readings. The system can also retrieve the patient's ECG data that were taken under similar circumstances and can analyze this subset of ECG data.

Figure 4:
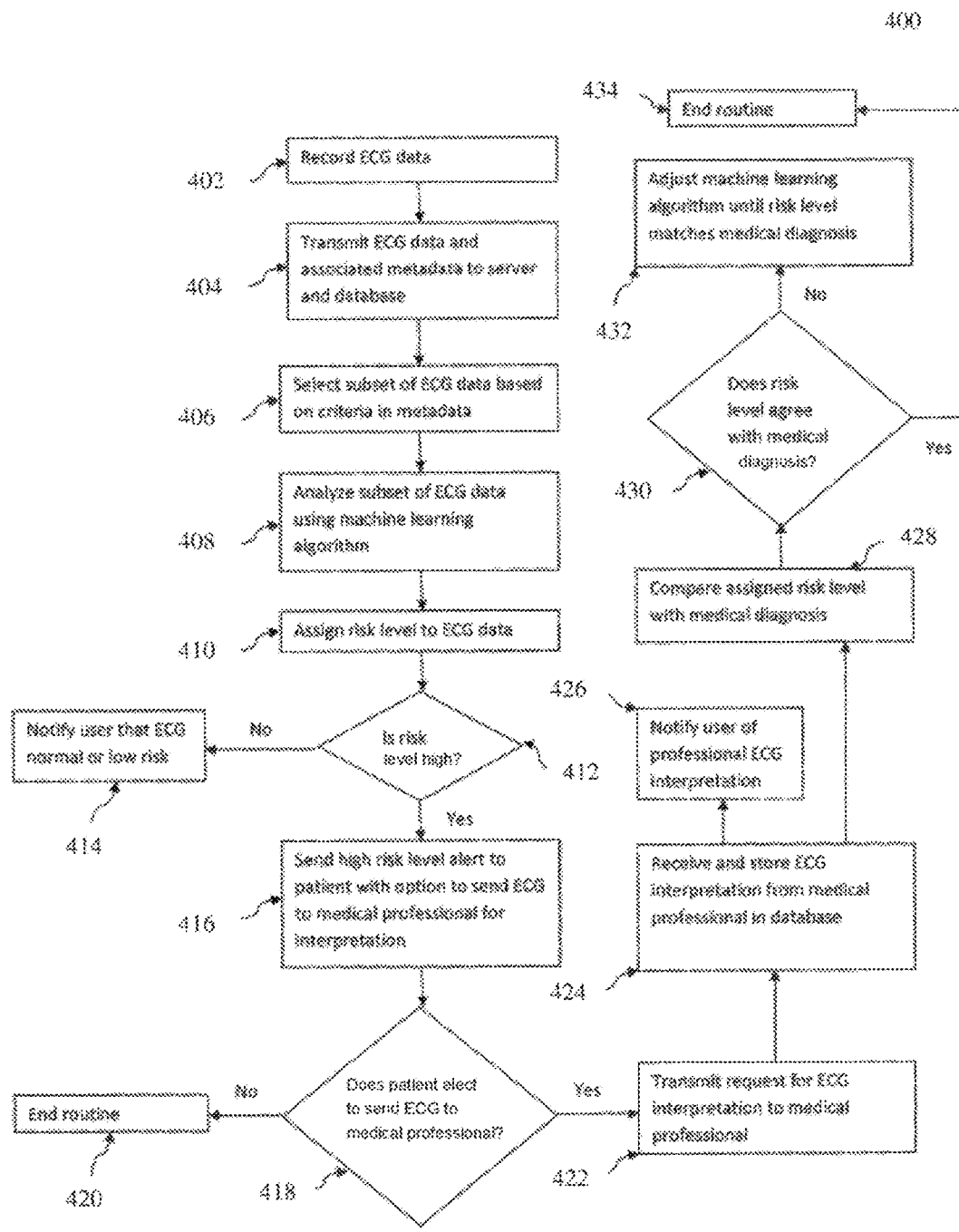
FIG. 4 shows an embodiment of the system and method of the ECG monitoring described herein.

FIG. 4 illustrates an embodiment of the system and method 400 of ECG monitoring described herein. The system can be implemented on a server or computer having a processor for executing the instructions described herein, which can be stored in memory. In step 402, ECG data can be recorded using any of the devices described herein for one or more patients. In step 404, the ECG data is transmitted along with associated metadata to a server and database that stores the ECG data. In step 406, a subset of the ECG data can be selected based on criteria in the metadata, such as user identity, time, device used to record the ECG data, and the like. In step 408, the subset of ECG data can be analyzed using a machine learning algorithm, which can assign a risk level to the ECG data in step 410. The system can then determine whether the risk level is high, as shown in step 412. If the risk level is low, the user can be notified that the ECG is normal or low risk, as shown in step 414. If the risk level is high, a high risk level alert can be sent to the patient with the option of sending the ECG to the medical professional for interpretation, as shown in step 416. The system then waits for the user's response to determine whether the patient elects to send the ECG to the medical professional for interpretation, as shown in step 418. If the patient does not wish to send the ECG to the medical professional for interpretation, the system can end the routine at this point, as shown in 420. If the patient does elect to send the ECG to the medical professional for interpretation, the request can be transmitted to the medical professional in step 422. The request to the medical professional can be sent to a workflow auction system as described in U.S. Provisional Application No. 61/800,879, filed Mar. 15, 2013, which is herein incorporated by reference in its entirety for all purposes. Once the medical professional has interpreted the ECG, the system can receive and store the ECG interpretation from the medical professional in the database, as shown in step 424. The system can then notify the user of the professional ECG interpretation, which can be sent to or accessed by the user, as shown in step 426. Additionally, the system can compare the assigned risk level with the medical diagnosis in step 428 and can determine whether the risk level determined by the system agrees with the medical diagnosis in step 430. If the risk level does not agree with the medical diagnosis, the machine learning algorithm can be adjusted until the risk level matches the medical diagnosis, as shown in step 432. If the risk level does agree with the medical diagnosis, the routine can be ended as shown in step 434.

Although the above steps show a method 400 in accordance with many embodiments, a person of ordinary skill in the art will recognize many variations based on the teaching described herein. The steps may be completed in a different order. Steps may be added or deleted. Some of the steps may comprise sub-steps. Many of the steps may be repeated as often as beneficial to the user or subject.

One or more of the steps of a method 400 may be performed with circuitry, for example, one or more of a processor or a logic circuitry such as a programmable array logic for a field programmable gate array. The circuitry may be programmed to provide one or more of the steps of a method 400, and the program may comprise program instructions stored on a non-transitory computer readable medium or memory or programmed steps of the logic circuitry such as the programmable array logic or the field programmable gate array, for example.

Aspects of the present disclosure provide systems and methods for generating a heart health score in response to continuously measured or monitored physiological parameter(s). The score may be given a quantitative value such as be graded from A to F or 0 to 100 for example (e.g. a great score may be an A or 100, a good score may be a B or 75, a moderate score may be a C or 50, a poor score may be a D or 25, and a failing score may be an F or 0.) If an arrhythmia is detected, the score may be below 50 for example. Other scoring ranges such as A to Z, 1 to 5, 1 to 10, 1 to 1000, etc. may also be used. Arrhythmia may be detecting using the machine learning based operations or algorithms described herein.

Figure 5:
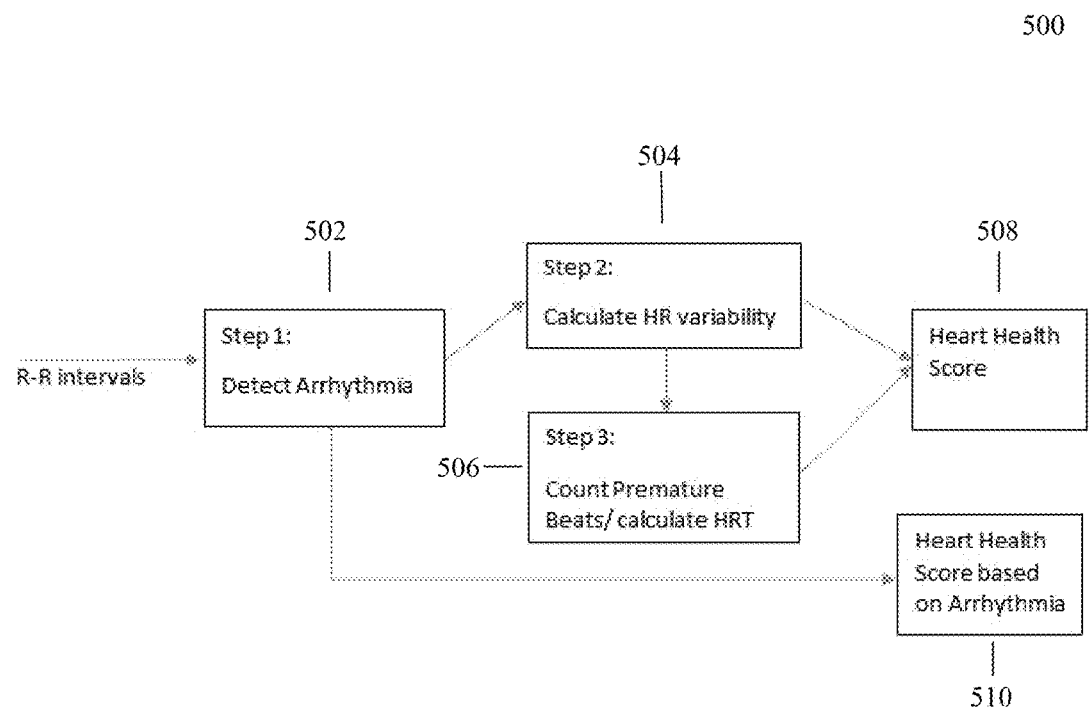
FIG. 5 shows a flow chart of an exemplary method to generate a heart health score in accordance with many embodiments.

FIG. 5 shows a flow chart of an exemplary method 500 to generate a heart health score in accordance with many embodiments.

In a step 502, an arrhythmia is detected. If an arrhythmia is detected (e.g. using the methods and/or algorithms disclosed herein), then the heart health score generated will be below 50. Depending on the severity of the arrhythmia detected, the heart score may be calculated or assigned within the ranges according to the table below in Table 2.

TABLE 2

| Arrhythmia | Heart Health score |
| --- | --- |
| ATRIAL FIBRILLATION, HR below 100 | 30-45 |
| ATRIAL FIBRILLATION, HR above 100 | 15-30 |
| Sinus Tachycardia | 20-40 |
| Supraventricular Tachycardia | 20-40 |
| Bradycardia | 20-40 |
| Bigeminy, Trigeminy | 30-50 |
| Short runs of High Heart Rate (VTACH suspect) | 10-30 |

In a step 504 a Heart Rate Variability (HRV) is calculated. HRV can be an indicator of heart health. The value for HRV value for a healthy heart is typically higher than HRV for an unhealthy heart. Also, HRV typically declines with age and may be affected by other factors, like stress, lack of physical activity, etc. HRV may be measured and analyzed using the methods described above. HRV may be calculated in the absence of arrhythmia, which may improve the accuracy of the HRV measurement. HRV may be determined and further analyzed as described above.

In a step 506, premature beats are counted and Heart Rate Turbulence (HRT) is calculated. Premature beats in the sequence of R-R intervals may be detected. Also, R-R intervals typically tend to recover at a certain pace after a premature beat. Using these two parameters (prematurity and pace of R-R recovery), HRT parameters may be calculated. There may be known deviations of HRT parameters associated with patients with risk of Congestive Heart Failure (CHF). These deviations, however, may be used to estimate an inverse measure. The number of premature beats per day (or per hour) may also be used as a measure of heart health. A low number of premature beats may indicate better heart health. In summary, the heart health score may be generated by combining at least heart rate variability (HRV), the number of premature beats, and heart rate turbulence (HRT). This combination (in the absence of arrhythmia) may provide an accurate estimate of how healthy the heart of the user is.

In a step 508, a heart health score is generated, and in a step 510, a hearth health score is generated based on an arrhythmia. To initially generate the score, a few hours (e.g. 2-5 hours) of measured R-R intervals may be required. A more accurate score may be generated after a week of continuous R-R interval measurements. Longer data sets may be required to detect significant arrhythmias as they may usually be detected within the first 7-8 days of monitoring.

Although the above steps show a method 500 in accordance with many embodiments, a person of ordinary skill in the art will recognize many variations based on the teaching described herein. The steps may be completed in a different order. Steps may be added or deleted. Some of the steps may comprise sub-steps. Many of the steps may be repeated as often as beneficial to the user or subject.

One or more of the steps of a method 500 may be performed with circuitry, for example, one or more of a processor or a logic circuitry such as a programmable array logic for a field programmable gate array. The circuitry may be programmed to provide one or more of the steps of a method 500, and the program may comprise program instructions stored on a non-transitory computer readable medium or memory or programmed steps of the logic circuitry such as the programmable array logic or the field programmable gate array, for example.

Figure 6:
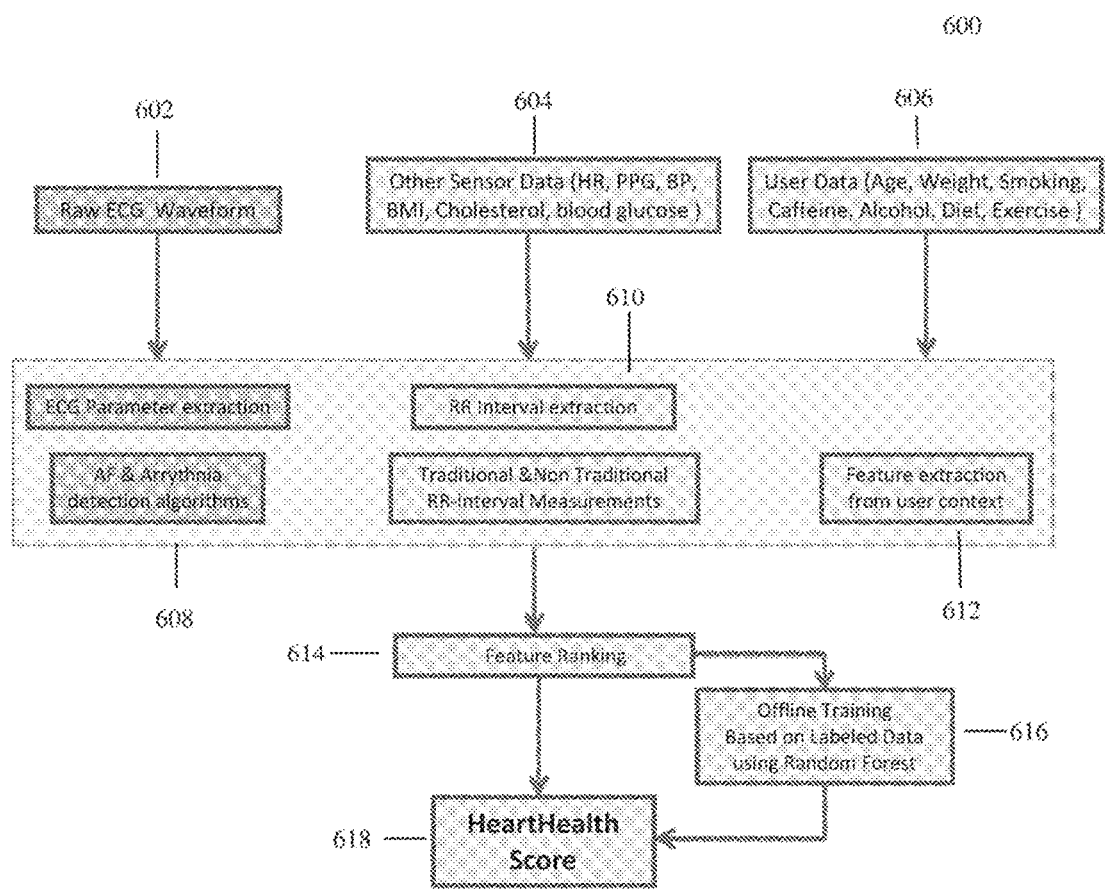
FIG. 6 shows an exemplary method of generating a heart score.

FIG. 6 shows a further method 600 of generating a heart score. In addition to the parameters which may be derived from the heart rate data described above, the heart health score may also be generated in response to further physiological parameters as shown in FIG. 6.

In a step 602, a raw ECG waveform is obtained. In a step 608, ECG parameters are extracted from the raw ECG waveform data and arrhythmia prediction and/or detection algorithms are run to analyze the obtained raw ECG waveform data.

In a step 604, physiological parameters may be measured using a sensor of the user's local computing device or an accessory thereof. Such measured physiological parameters may include blood pressure, user activity and exercise level, blood oxygenation levels, blood sugar levels, an electrocardiogram, skin hydration or the like of the user. These physiological parameters may be measured over time such as over substantially the same time scale or length as the measurement of heart rate. In a step 610, an R-R interval is extracted and both traditional and non-traditional heart rate measures are used to analyze the measured heart rate and physiological parameters.

In a step 606, additional physiological parameters for determining the heart health score may be input by the user. These parameters may include the age, the gender, the weight, the height, the body type, the body mass index (BMI), the personal medical history, the family medical history, the exercise and activity level, the diet, the hydration level, the amount of sleep, the cholesterol level, the alcohol intake level, the caffeine intake level, the smoking status, and the like of the user. For example, the heart health score may be weighted by age and/or gender to provide the user an accurate assessment of his or her heart health in response to the heart rate data. In a step 612, feature extraction is used to analyze the inputted physiological parameters.

In a step 614 feature ranking and/or feature selection occurs. In a step 618, a real time prediction or detection of atrial fibrillation, and/or in a step 616, the heart rate variability measurements may be labelled and saved for offline training of a machine learning algorithm or set of machine learning operations, and then may be subsequently used to make a real time prediction and/or detection of atrial fibrillation. A plurality of heart health scores may be generated by a plurality of users to generate a set of population data. This population data may be used to train the machine learning algorithms described herein such that the trained algorithm may be able to detect and predict atrial fibrillation or other health conditions from user data.

Although the above steps show a method 600 in accordance with many embodiments, a person of ordinary skill in the art will recognize many variations based on the teaching described herein. The steps may be completed in a different order. Steps may be added or deleted. Some of the steps may comprise sub-steps. Many of the steps may be repeated as often as beneficial to the user or subject.

One or more of the steps of a method 600 may be performed with circuitry, for example, one or more of a processor or a logic circuitry such as a programmable array logic for a field programmable gate array. The circuitry may be programmed to provide one or more of the steps of a method 600, and the program may comprise program instructions stored on a non-transitory computer readable medium or memory or programmed steps of the logic circuitry such as the programmable array logic or the field programmable gate array, for example.

The systems and methods for generating a heart health score in response to continuously measured or monitored physiological parameter(s) may comprise a processor of a computing device and software. A processor of a computing device (e.g. a tablet computer, a smartphone, a smart watch, a smart band, a wearable computing device, or the like) may execute this set of instructions to receive the input data and detect and/or predict atrial fibrillation therefrom. The software may be downloaded from an online application distribution platform such as the Apple iTunes or App Store, Google Play, Amazon App Store, and the like. A display of the computing device may notify the user of the calculated heart health score and/or if further measurements are required (e.g. to perform a more accurate analysis).

Figure 7:
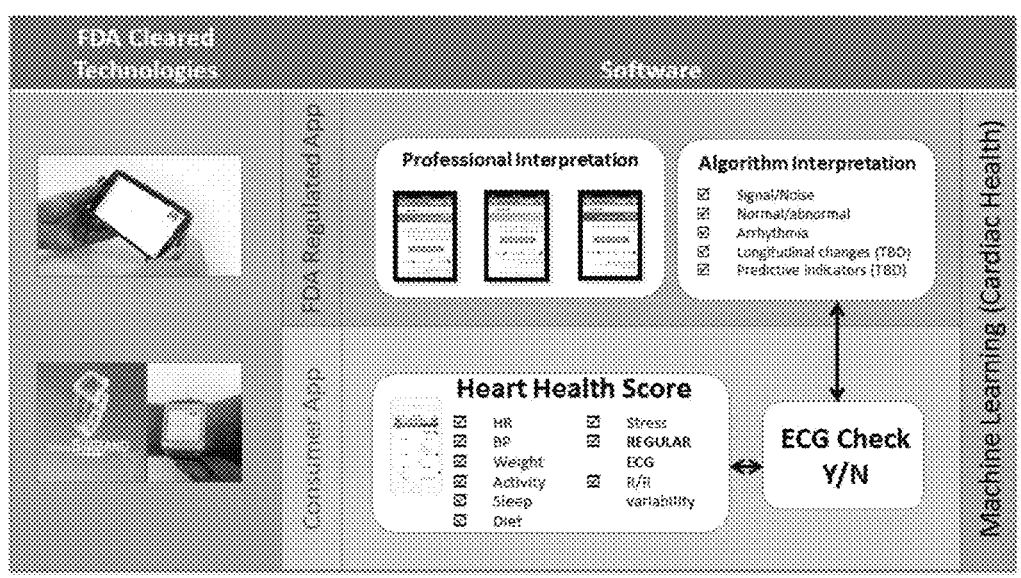
FIG. 7 shows a schematic diagram of the executed application described herein.

FIG. 7 shows a schematic diagram of the executed application described herein. The heart health score may be provided on a software application such as a mobile app downloaded from an application distribution platform and executed on a local computing device of the user as described above. This executed application may instruct the user to take active steps in response to a poor or moderate heart health score. For example, the instructions to the user may be to make a corrective measure such as to modify his or her diet, exercise pattern, sleep pattern, or the like. Alternatively or in combination, the instructions to the user may be to take a further step such as to take an electrocardiogram (e.g. to verify the presence of an arrhythmia), enroll in an electrocardiogram over-read service, or schedule an appointment with a physician or other medical specialist. If the heart health score is below a desired threshold for good heart health, the executed application may link the user to a second execute application with further application features. Alternatively or in combination, these further features may be unlocked on the first executed application if the heart health score is below the threshold. In at least some cases, a prescription or verification from a medical professional may also be required to unlock the further application features.

Figure 8:
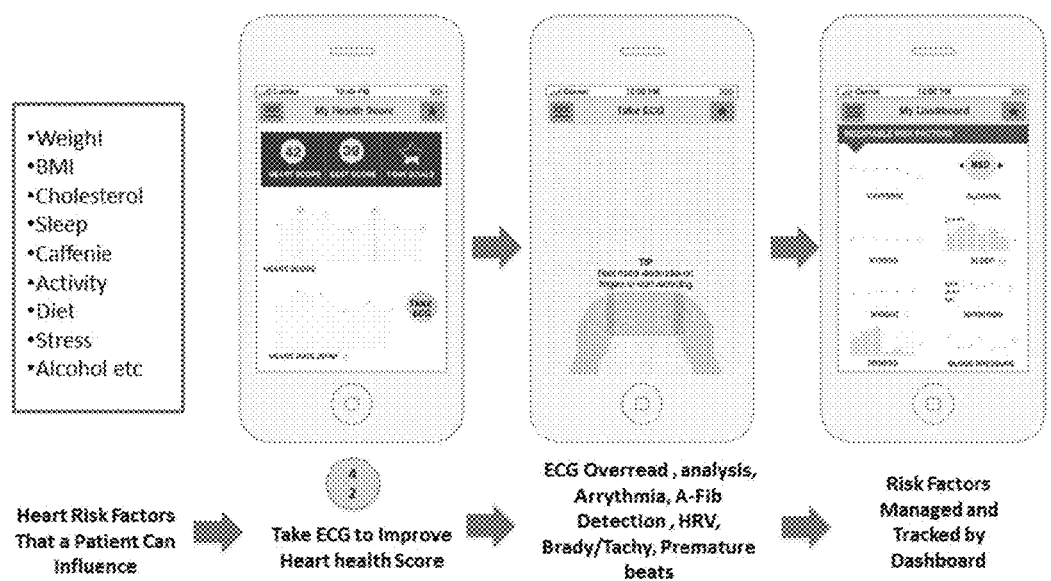
FIG. 8 shows exemplary screenshots of the executed application.

FIG. 8 shows screenshots of the executed application. The further features unlocked may include the ability to read electrocardiogram (ECG) data from a sensor coupled to the local computing device and display the electrocardiogram (ECG) in real-time and/or detect and alert for atrial fibrillation based on the electrocardiogram (ECG) in real-time (e.g. as described in U.S. application Ser. Nos. 12/796,188, 13/108,738, 13/420,540, and 13/964,490). As shown in FIG. 8, these further features may include an electrocardiogram (ECG) over-read service such as that described in U.S. application Ser. No. 14/217,032. The first executed application may comprise a consumer software application and the second executed application may comprise a medical professional or regulated software application or set of features of the first executed application. As described herein and shown in FIG. 8, the executed application may provide a dash board to track the heart health of the user and show risk factors which may be monitored and tracked by the user. The dash board may be provided with further features such as that described in U.S. Ser. No. 61/915,113 (filed Dec. 12, 2013).

Figure 9:
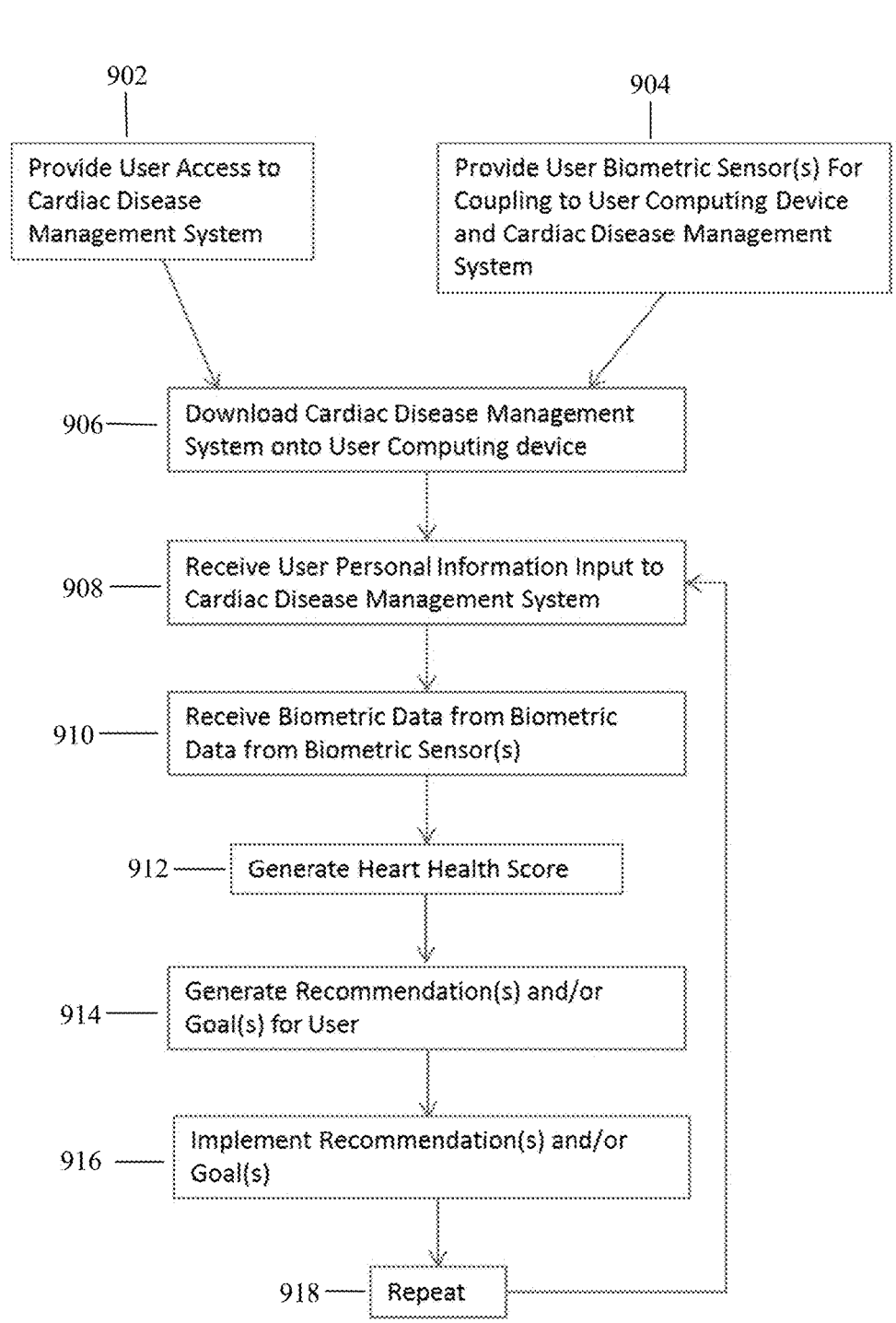
FIG. 9 shows an exemplary method for cardiac disease and rhythm management.

FIG. 9 shows a method 900 for cardiac disease and rhythm management, which may, for example, be implemented with the system 100 described herein. In a step 902, a user or subject is provided access to a cardiac disease and/or rhythm management system such as system 100. Step 902 may comprise prescribing the use of the system 100 for the user or subject. In a step 904, the user or subject is provided one or more biometric sensors. These biometric sensor(s) may couple to a computing device of the user or subject, e.g. a personal desktop computer, a laptop computer, a tablet computer, a smartphone, etc., and associated software loaded thereon.

In a step 906, the user or subject downloads the cardiac disease and/or rhythm management system software onto their computing device. For example, the system software may comprise a mobile software application ("mobile app") downloaded from the Apple App Store, Google Play, Amazon Appstore, BlackBerry World, Nokia Store, Windows Store, Windows Phone Store, Samsung Apps Store, and the like. The downloaded system software, e.g. mobile app 101a, may be configured to interface with the biometric sensors provided to the user or subject in the step 154.

In a step 908, personal information input to the cardiac disease management system is received. For example, the user or subject may enter his or her gender, height, weight, diet, disease risk factors, etc. into the mobile app 101a. Alternatively or in combination, this personal information may be input on behalf of the user or subject, for example, by a physician of the user or subject.

In a step 910, biometric data is received from the biometric sensors provided to the user or subject. For example, the system 100 and the mobile app 101a may receive ECG data and heart rate from handheld sensor 103, activity data from wrist-worn activity sensor 105, blood pressure and heart rate data from mobile blood pressure monitor 107a, and other data such as weight and body fat percentage data from a "smart" scale in communication with the local computing device 101.

In a step 912, a cardiac health score is generated. The cardiac health score can be generated by considering and weighing one or more influencing factors including the incidence of atrial fibrillation or arrhythmia as detected by the handheld ECG monitor, the heart rate of the user or subject, the activity of the user or subject, hours of sleep and rest of the user or subject, blood pressure of the user or subject, etc. Often, the incidence of atrial fibrillation or arrhythmia will be weighed the most. The cardiac health score may be generated by a physician or a machine learning algorithm provided by the remote server or cloud-based service 113, for example. A plurality of users and subject may concurrently use the cardiac health and/or rhythm management system 100 and the machine learning algorithm may, for example, consider population data and trends to generate an individual user or subject's cardiac health score.

In a step 914, one or more recommendations or goals is generated for the user or subject based on or in response to the generated cardiac health score. These recommendation(s) and/or goal(s) may be generated automatically based on or in response to the biometric and personal information of the user or subject. For example, the machine learning algorithm may generate these recommendation(s)/goal(s). Alternatively or in combination, a physician or other medical specialist may generate the recommendation(s) and/or goal(s), for example, based on or in response to the biometric and personal information of the user or subject. The physician or other medical professional may access the patient data through the Internet as described above.

In a step 916, the patient implements many if not all of the recommendation(s) and/or goal(s) provided to him or her. And in a step 916, steps 908 to 916 may be repeated such that the user or subject may iteratively improve their cardiac health score and their overall health.

Although the above steps show method 900 of managing cardiac disease and/or rhythm in accordance with many embodiments, a person of ordinary skill in the art will recognize many variations based on the teaching described herein. The steps may be completed in a different order. Steps may be added or deleted. Some of the steps may comprise sub-steps. Many of the steps may be repeated as often as beneficial to the user or subject.

One or more of the steps of the method 900 may be performed with circuitry, for example, one or more of a processor or a logic circuitry such as a programmable array logic for a field programmable gate array. The circuitry may be programmed to provide one or more of the steps of the method 900, and the program may comprise program instructions stored on a non-transitory computer readable medium or memory or programmed steps of the logic circuitry such as the programmable array logic or the field programmable gate array, for example.

In some embodiments, the heart rate information (or an extracted portion of HR information) may be used to compare to a database of similar information that has been correlated with cardiac events. For example, heart rate information may be compared to a database of HR information extracted for ECG recordings of patients known to be experiencing cardiac problems. Thus, patterns of heart rate information taken from a subject may be compared to patterns of cardiac information in a database. If there is a match (or a match within a reasonable closeness of fit), the patient may be instructed to record an ECG, e.g. using an ambulatory ECG monitor. This may then provide a more detailed view of the heart. This method may be particularly useful, as it may allow recording and/or transmission and/or analysis of detailed electrical information about the heart at or near the time (or shortly thereafter) when a clinically significant cardiac event is occurring. Thus, the continuous monitoring may allow a subject to be alerted immediately upon an indication of the potential problem (e.g. an increase in HRV suggestive of a cardiac dysfunction). This may allow the coupling of continuous HR monitoring with ECG recording and analysis for disease diagnosis and disease management.

Figure 10:
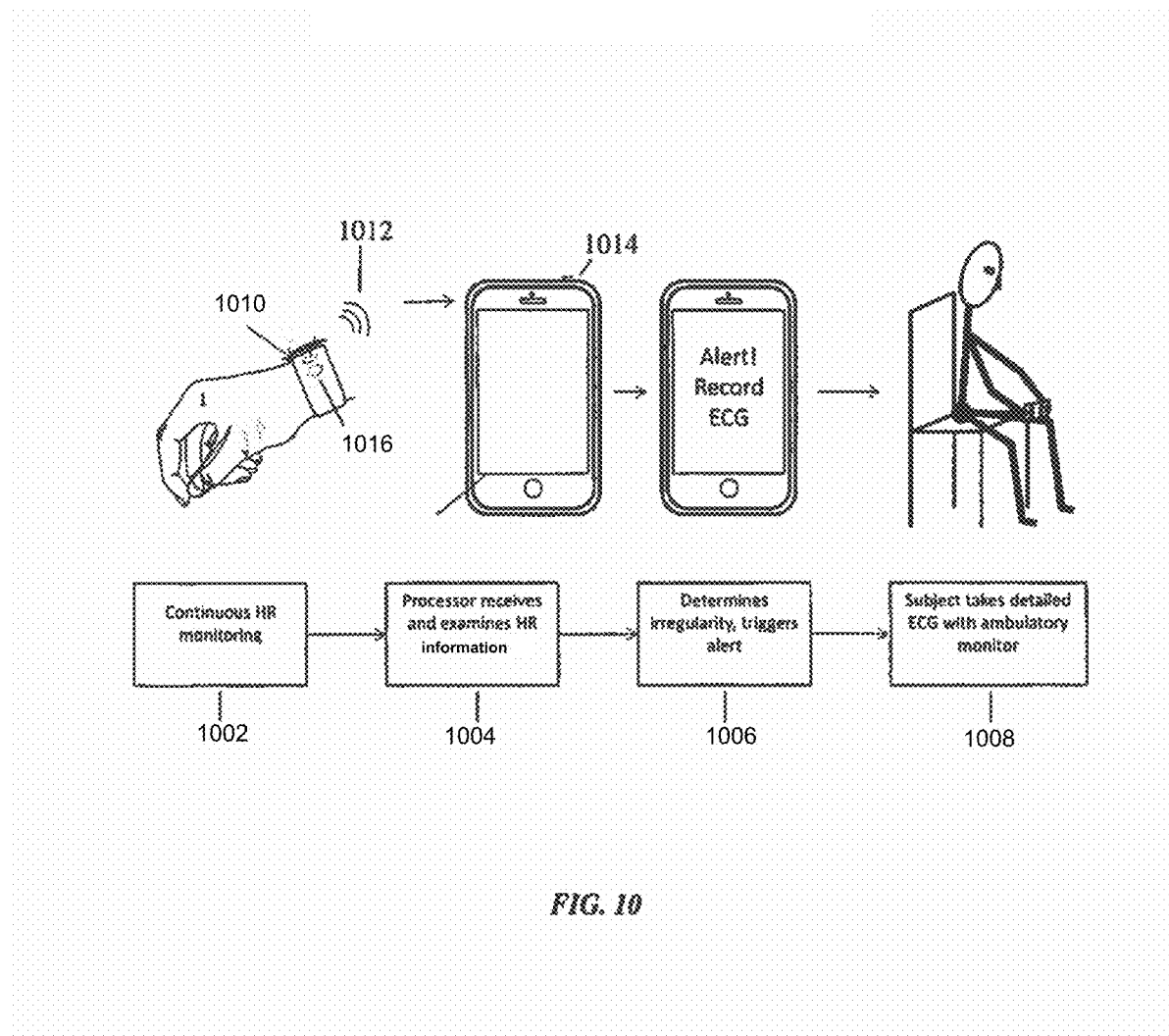
FIG. 10 shows an exemplary method for monitoring a subject to determine when to record an electrocardiogram (ECG)

FIG. 10 illustrates one variation of a method for monitoring a subject to determine when to record an electrocardiogram (ECG). In FIG. 10, a subject is wearing a continuous heart rate monitor (configured as a watch 1010, including electrodes 1016), shown in step 1002. The heart rate monitor transmits (wirelessly 1012) heart rate information that is received by the smartphone 1018, as shown in step 1004. The smartphone includes a processor that may analyze the heart rate information 1004, and when an irregularity is determined, may indicate 1006 to the subject that an ECG should be recorded. In FIG. 10, an ambulatory ECG monitor 1014 is attached (as a case having electrodes) to the phone 1018. The user may apply the ECG monitor as to their body (e.g. chest, between arms, etc.) 1008 to record ECGs that can then be saved and/or transmitted for analysis.

Figure 11:
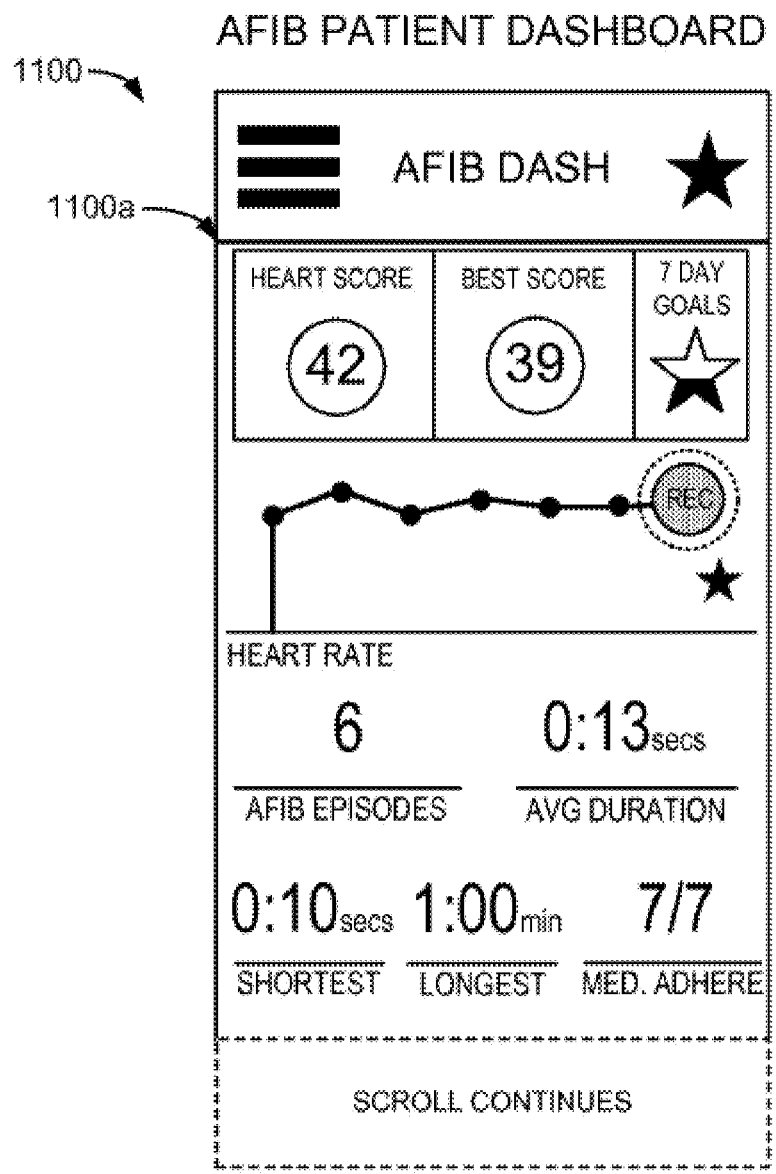
FIG. 11 shows an exemplary screenshot of a first aspect of a dashboard application.
Figure 11A:
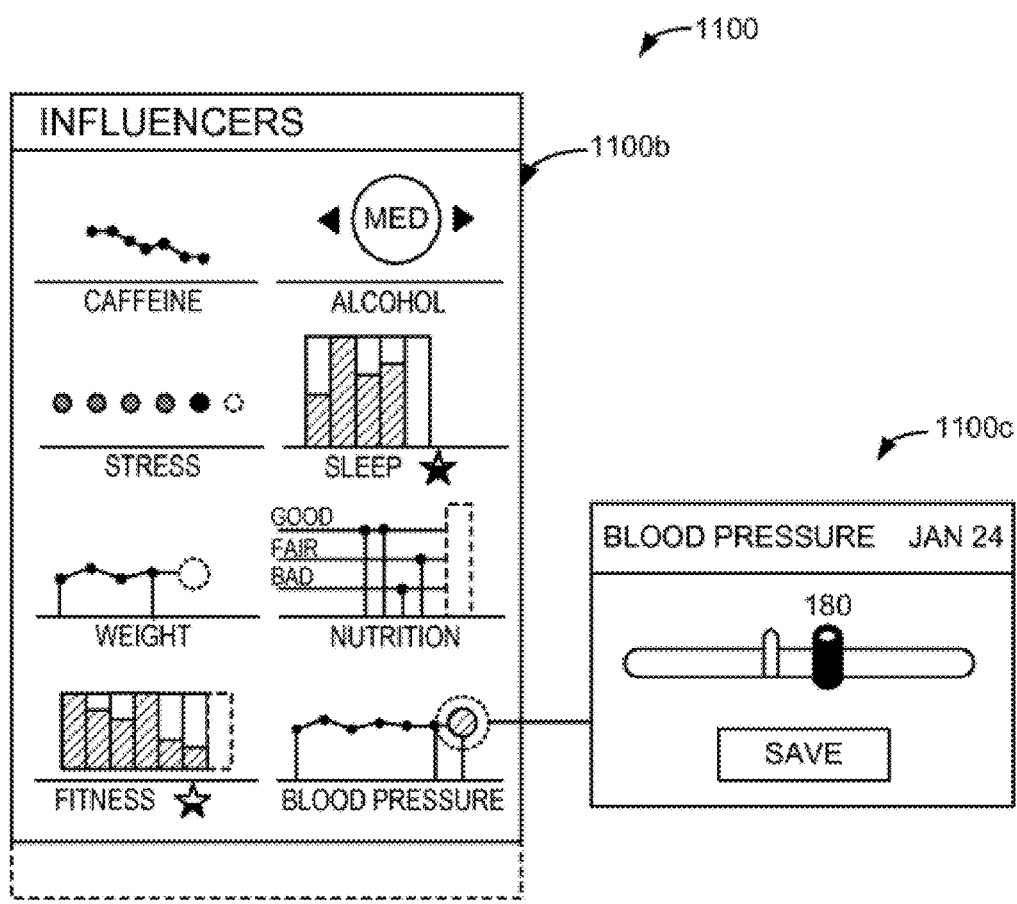
FIG. 11A shows an exemplary screenshot of a second aspect of a dashboard application.

FIGS. 11 and 11A show screenshots of an atrial fibrillation dashboard 1100 of a user interface for the cardiac disease and/or rhythm management system 100. FIG. 11 shows a top portion 1100a of the atrial fibrillation dashboard 1100 while FIG. 10A shows a bottom portion 1100b of the atrial fibrillation dashboard 1100.

The top portion 1100a of the atrial fibrillation dashboard 1100 as shown in FIG. 10 may display the current cardiac health score of the user or subject, a recent best cardiac health score of the user or subject, and a completion percentage of recommendation(s) and/or goal(s) for the user or subject. The user or subject may tap any one of the cardiac health score displays or the recommendation(s) and/or goal (s) displays to access more detailed information regarding the calculated health score(s) or recommendation(s) and/or goal(s), respectively. The top portion 1100a may also show an ECG of the user or subject and a button which may be tapped to record the ECG of the user or subject for the day. As discussed with reference to FIG. 1, the ECG may be recorded with a handheld sensor 103 in communication with the local computing device 100. The top portion 1000a may also show the number of atrial fibrillation episodes and the average duration of these atrial fibrillation episodes. This number and duration may be generated automatically by software or logic of the mobile app 101a based on or in response to the ECG measurements taken by the user or subject. Alternatively or in combination, a physician may access the atrial fibrillation dashboard 1100 of an individual user or subject, evaluate his or her ECGs, and provide the number of atrial fibrillation episodes and their duration to the mobile app 101a or other software loaded on the local computing device 101 of the user or subject. The shortest and longest durations of the atrial fibrillation episodes may also be shown by the top portion 1100a as well as the user or subject's daily adherence to a medication regime.

The bottom portion 1100b of the atrial fibrillation dashboard 1100 as shown in FIG. 10A may display one or more influencers which influence how the cardiac health score is generated. These influencers may include, for example, caffeine intake, alcohol intake, stress levels, sleep levels, weight, nutrition, fitness and activity levels, and blood pressure. Data for these influencers may be input automatically by one or more biometric sensors coupled to the local computing device 101 and/or the mobile app 101a. Alternatively or in combination, the data for these influencers may be input manually by the user or subject by tapping on the respective influencer display. For example, tapping on the blood pressure display area may cause a slider input 1100c for blood pressure to pop up. The user or subject may use the slider to enter and save his or her blood pressure for the day. Similar pop-ups or user-selected inputs may be provided for the other influencers. For example, the user or subject may enter his or her daily caffeine or alcohol intake, stress and sleep levels, nutrition levels, or activity and fitness levels (e.g. low/bad, medium/so-so, or high/good based on the user's age, gender, height, weight, etc. as can be indicated by an instruction page of the mobile app 101a). The influencer displays may also show the goal progression of the user or subject.

Figure 12:
FIG. 12 shows an exemplary screenshot of a first aspect of a goals and recommendations page of the cardiac disease and rhythm management system interface or mobile app.
Figure 12A:
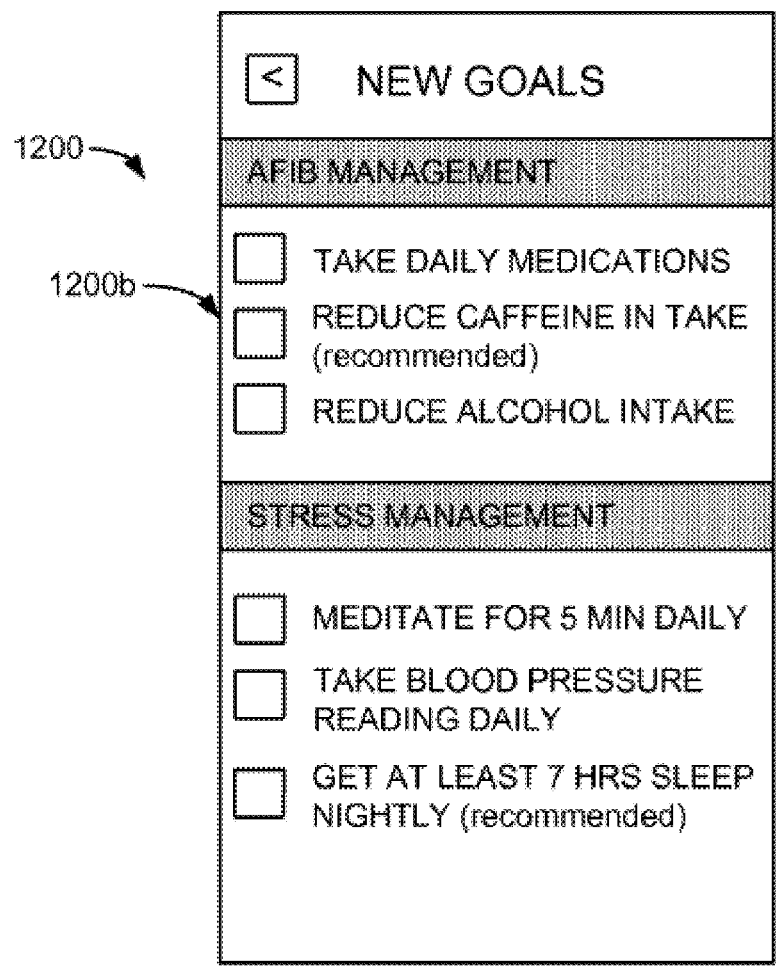
FIG. 12A shows an exemplary screenshot of a second aspect of a goals and recommendations page of the cardiac disease and rhythm management system interface or mobile app.

FIGS. 12 and 12A show screenshots of a goals and recommendations page 1200 of the cardiac disease and rhythm management system interface or mobile app 101a. A top portion 1200a of the goals and recommendations page 1100 may comprise a listing of 7-day goals for the user or subject. The top portion 1200a may further comprise every-day goals for the user or subject which often cannot be removed or changed. The user or subject can check off these goals or recommendations as he or she meets them. The top portion 1200a may track goal completion percentage over a 7-day period. The user or subject can set the same goals for the next day and/or set new goals.

A bottom portion 1200b of the goals and recommendations page 1200 may comprise a listing of new goals which the user or subject may add. The new goals may be categorized into goals or recommendations for atrial fibrillation management, stress management, and/or other categories. For example, goals for atrial fibrillation management may include taking daily medications, reducing caffeine intake, and reducing alcohol intake. And, goals for stress management may include meditate for 5 minutes daily, take blood pressure reading daily, and getting at least 7 hours of sleep nightly. Using the goals and recommendations page 1200, the user or subject can set their goals for the week. One or more of these goals may be automatically recommended to the user or subject or be recommended by a physician having access to the dashboard 1100. For example, goals may be recommended based on last week's progress. The completion of recommended goals can result in the user or subject earning more "points," in effect gamifying health and cardiac rhythm management for the user or subject. Alternatively or in combination, the goals may be set by a physician having access to the dashboard 1100.

Figure 13:
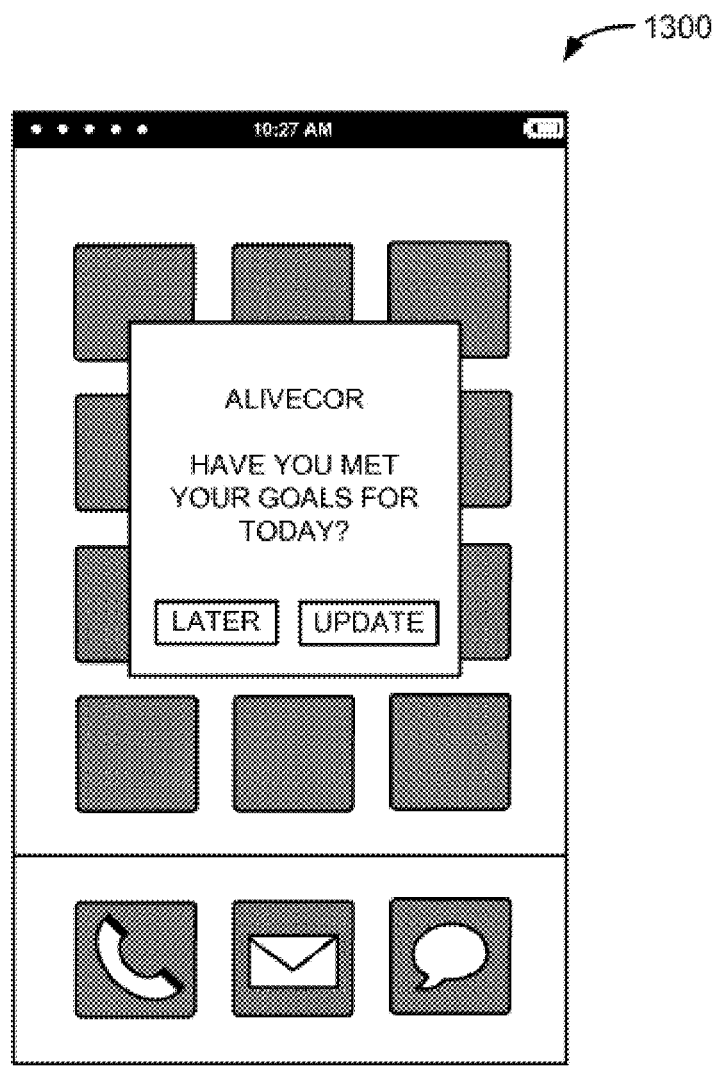
FIG. 13 shows an exemplary screenshot of a user's local computing device notifying the user with a pop-up notice to meet their daily recommendations and goals.

FIG. 13 shows a screenshot of a user's local computing device notifying the user with a pop-up notice 1300 to meet their daily recommendations and goals. By tapping on the pop-up notice, 1300, the user or subject can be taken to the atrial fibrillation dashboard where the user or subject can update or otherwise manage their cardiac health.

Figure 14:
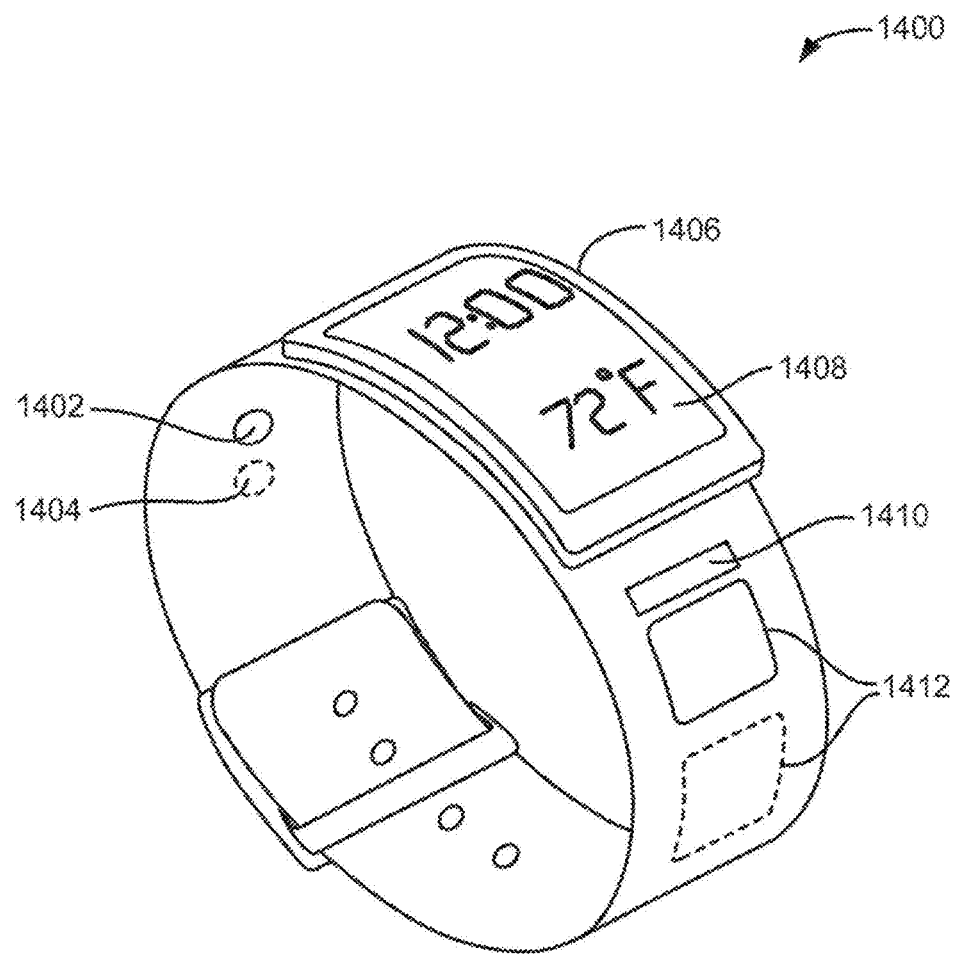
FIG. 14 shows an embodiment comprising a smart watch which includes at least one heart rate monitor and at least one activity monitor.

FIG. 14 shows an embodiment comprising a smart watch 1400 which includes at least one heart rate monitor 1402 and at least one activity monitor 1404. One or more processors are coupled to one or more non-transitory memories of the smart watch and configured to communicate with the heart rate monitor 1402 and the activity monitor 1404. The one or more processors are further coupled to an output device 1408. Processor executable code is stored on the one or more memories and when executed by the one or more processors causes the one or more processors to determine if heart rate and activity measurements represent an advisory condition for recording an ECG, and generate and send notification signals through the output device 1408 when an advisory condition for recording an ECG is determined.

For example, presently available smart watches include motion sensors such as pedometers. Pedometers can be based on an accelerometer or electromechanical mechanism such as a pendulum, magnetic reed proximity switch, and a spring suspended lever arm with metal-on-metal contact. Modern accelerometers are often small micro electro-mechanical systems and are well known by those skilled in the art. Heart rate monitors are readily available with smart phones as well as smart watches. One type uses an optical sensor to detect the fluctuation of blood flow. The signal can be amplified further using, for example, a microcontroller to count the rate of fluctuation, which is actually the heart rate.

An advisory condition for recording an ECG may occur due to, for example, large continuing fluctuations in heart rate. An advisory condition for recording an ECG can also occur when a measured heart rate increases rapidly without a corresponding increase in activity monitored by, for example, an accelerometer. By comparing measured heart rate changes with measured activity changes, the presently disclosed software or "app" minimizes false alarms are minimized. ECG devices are described in U.S. Ser. No. 12/796,188, filed Jun. 8, 2010, now U.S. Pat. No. 8,509,882, hereby expressly incorporated herein by reference in its entirety. The ECG device can be present in a smart watch band or a smart phone. In one embodiment, the ECG device includes an electrode assembly configured to sense heart-related signals upon contact with a user's skin, and to convert the sensed heart-related signals to an ECG electric signal. The ECG device transmits an ultrasonic frequency modulated ECG signal to a computing device such as, for example, a smartphone. Software running on the computing device or smartphone digitizes and processes the audio in real-time, where the frequency modulated ECG signal is demodulated. The ECG can be further processed using algorithms to calculate heart rate and identify arrhythmias. The ECG, heart rate, and rhythm information can be displayed on the computer or smartphone, stored locally for later retrieval, and/or transmitted in real-time to a web server via a 2G/3G/4G, WiFi or other Internet connection. In addition to the display and local processing of the ECG data, the computer or smartphone can transmit, in real-time, the ECG, heart rate and rhythm data via a secure web connection for viewing, storage and further analysis via a web browser interface.

In another embodiment, the converter assembly of an ECG device is integrated with, and electrically connected to the electrode assembly and is configured to convert the electric ECG signal generated by electrode assembly to a frequency modulated ECG ultrasonic signal having a carrier frequency in the range of from about 18 kHz to about 24 kHz. It is sometimes desirable to utilize a carrier frequency in the 20 kHz to 24 kHz range. The ultrasonic range creates both a lower noise and a silent communication between the acquisition electronics and the computing device such as the smartphone, notebook, smart watch and the like.

A kit can include downloadable software such as an "app" for detecting an advisory condition for recording an ECG and an ECG device. The ECG device can be present on a watch band for replacing a specific band on a smart watch. The ECG device can also be provided on a smart phone back plate for replacing an existing removable smartphone back. In another configuration, the ECG device is usable as a smartphone protective case.

Software on the smartphone or smart watch can also combine data and signals from other sensors built into the smartphone or smart watch such as a GPS.

While preferred embodiments of the present disclosure have been shown and described herein, it will be obvious to those skilled in the art that such embodiments are provided by way of example only. Numerous variations, changes, and substitutions will now occur to those skilled in the art without departing from the subject matter described herein. It should be understood that various alternatives to the embodiments of the subject matter described herein may be employed in practicing the subject matter described herein. It is intended that the following claims define the scope of the disclosure and that methods and structures within the scope of these claims and their equivalents be covered thereby.

What is claimed is:

1. A smart watch to detect a presence of an arrhythmia of a user, comprising:
 a processing device;
 a photoplethysmography ("PPG") sensor operatively coupled to the processing device;
 a motion sensor operatively coupled to the processing device; and
 a memory operatively coupled to the processing device, the memory having instructions stored thereon that, when executed by the processing device, cause the processing device to:
  receive a raw PPG waveform signal from the PPG sensor;
  extract a heartrate variability ("HRV") signal from the raw PPG waveform signal;
  receive motion sensor data from the motion sensor;
  generate activity level data based on the received motion sensor data;
  input the HRV signal and the activity level data into a machine learning algorithm trained to detect arrhythmias;
  detect, by the machine learning algorithm, the presence of the arrhythmia; and
  generate a notification of the detected arrhythmia.

2. The smart watch according to claim 1, wherein the processing device is further to:
 extract one or more features from the raw PPG waveform signal; and
 input the one or more features with the raw PPG waveform signal into the machine learning algorithm.

3. The smart watch according to claim 2, wherein the one or more features correspond to the HRV signal analyzed in a time domain.

4. The smart watch according to claim 3, Wherein the time domain corresponds to one of SDNN, SDANN, RMSSD, SDSD, NN50, pNN50, NN20, pNN20, EBC, NNx, or pNNx time domains.

5. The smart watch according to claim 2, wherein the one or more features comprise a nonlinear transform of R-R ratio or R-R ratio statistics with an adaptive weighting factor.

6. The smart watch according to claim 2, wherein the one or more features may be features of the HRV signal analyzed geometrically.

7. The smart watch according to claim 2, wherein the one or more features may be features of the HRV analyzed in a frequency domain.

8. The smart watch according to claim 2, wherein the one or more features may be non-linear features.

9. The smart watch according to claim 1, the smart watch further comprising a biometric data sensor, wherein the processing device is further to:
 receive biometric data of the user from the biometric data sensor; and
 input the biometric data with the raw PPG waveform signal into the machine learning algorithm.

10. The smart watch according to claim 9, wherein the biometric data comprises at least one of: a temperature, blood pressure, or inertial data of the user.

11. The smart watch according to claim 1, wherein the machine learning algorithm stores heart rate data and HRV data previously associated with arrhythmias in the user and detects the presence of the arrhythmia based on at least one of the stored heart rate data or the stored HRV data.

12. The smart watch according to claim 1, wherein the machine learning algorithm stores heart rate data and HRV data previously associated with arrhythmias in a second user and detects the presence of the arrhythmia of the user based on at least one of the stored heart rate data or the stored HRV data of the second user.

13. The smart watch according to claim 1, further comprising an electrocardiogram (ECG) sensor operatively coupled to the processing device, wherein the processing device is further to record an ECG using the ECG sensor.

14. The smart watch according to claim 13, the processing device further to input the ECG into the machine learning algorithm trained to detect arrhythmias.

15. The smart watch according to claim 13, the processing device further to record the ECG using the ECG sensor in response to receiving an indication of a user action.

16. The smart watch according to claim 13, wherein the processing device is further to notify the user of a predicted arrhythmia.

17. A method to detect a presence of an arrhythmia of a user, comprising:
  receiving, by a processing device, a photoplethysmography ("PPG") waveform signal from a PPG sensor;
  extracting a heartrate variability ("HRV") signal from the PPG waveform signal;
  inputting the HRV signal into a machine learning algorithm trained to detect arrhythmias;
  detecting, by the machine learning algorithm, the presence of the arrhythmia; and
  generating a notification of the detected arrhythmia.

18. The method according to claim 17, further comprising:
  generating a heartrate waveform signal based on the PPG waveform signal; and
  inputting the heartrate waveform signal into the machine learning algorithm with the PPG waveform signal.

19. The method according to claim 17, Wherein the PPG waveform signal is a raw PPG waveform signal, the method further comprising:
  extracting one or more features from the raw PPG waveform signal; and
  inputting the one or more features with the raw PPG waveform signal into the machine learning algorithm.

20. The method according to claim 17, further comprising recording an electrocardiogram (ECG) using an ECG.

21. The method according to claim 20, further comprising inputting the ECG into the machine learning algorithm.

22. The method according to claim 20, further comprising recording the ECG using the EGG sensor in response to receiving an indication of a user action.

23. The method according to claim 17, timber comprising:
  receiving a motion signal from a motion sensor; and
  inputting the motion signal into the machine learning algorithm trained to detect arrhythmias.

24. The method according to claim 17, further comprising notifying the user of a predicted arrhythmia.

25. A non-transitory computer-readable storage medium including instructions that, when executed by a processing device, cause the processing device to:
  receive heart rate variability (HRV) data;
  receive motion sensor data from a motion sensor;
  input the HRV data and the motion sensor data into a machine learning algorithm trained to detect arrhythmias;
  detect, by the machine learning algorithm, a presence of an arrhythmia; and
  notify a user of the detected arrhythmia.

26. The non-transitory computer-readable storage medium of claim 25, wherein the instructions further cause the processing device to:
  receive a raw photoplethysmography ("PPG") waveform signal from a PPG sensor;
  generate a heartrate waveform signal based on the raw PPG waveform signal; and
  input the heartrate waveform signal into the machine learning algorithm with the raw PPG waveform signal.

27. The non-transitory computer-readable storage medium of claim 25, wherein the instructions further cause the processing device to:
  receive a raw photoplethysmography ("PPG") waveform signal from a PPG sensor;
  extract the HRV data from the raw PPG waveform signal; and
  input the HRV data with the raw PPG waveform signal into the machine learning algorithm.

28. The non-transitory computer-readable storage medium of claim 25, wherein the instructions further cause the processing device to:
  receive a raw photoplethysmography ("PPG") waveform signal from a PPG sensor;
  extract one or more features from the raw PPG waveform signal; and
  input the one or more features with the raw PPG waveform signal into the machine learning algorithm.

29. The non-transitory computer-readable storage medium of claim 25, wherein the instructions further cause the processing device to record an electrocardiogram (ECG) using an ECG sensor.

30. The non-transitory computer-readable storage medium of claim 29, the processing device further to input the ECG into the machine learning algorithm.

31. The non-transitory computer-readable storage medium of claim 29, the processing device Maher to record the EGG using the ECG sensor in response to receiving an indication of a user action.

32. The non-transitory computer-readable storage medium of claim 25, wherein the instructions further cause the processing device to notify the user of the detected arrhythmia.

33. The non-transitory computer-readable storage medium of claim 25, wherein to input the motion sensor data into the machine learning algorithm, the instructions further cause the processing device to generate an activity level signal based on the motion sensor data.

* * * * *